United States Patent
Nazeeruddin et al.

(10) Patent No.: US 9,359,334 B2
(45) Date of Patent: Jun. 7, 2016

(54) LIGANDS FOR SENSITIZING DYES OF DYE-SENSITIZED SOLAR CELLS

(75) Inventors: Mohammad Khaja Nazeeruddin, Ecublens (CH); Michael Graetzel, St-Sulpice (CH); Alessandro Abbotto, Milan (IT); Chiara Marinzi, Bresso (IT); Norberto Manfredi, Cassina dei Pecchi (IT); Filippo De Angelis, Istituto di Scienze e Tecnologie Molecolari (IT)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 38 days.

(21) Appl. No.: 13/499,012

(22) PCT Filed: Sep. 29, 2010

(86) PCT No.: PCT/IB2010/054399
§ 371 (c)(1),
(2), (4) Date: Mar. 29, 2012

(87) PCT Pub. No.: WO2011/039715
PCT Pub. Date: Apr. 7, 2011

(65) Prior Publication Data
US 2012/0253043 A1    Oct. 4, 2012

(30) Foreign Application Priority Data

Sep. 29, 2009    (EP) ..................................... 09171711

(51) Int. Cl.
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 409/04 | (2006.01) |
| C07D 405/04 | (2006.01) |
| C07D 495/04 | (2006.01) |
| C07D 495/14 | (2006.01) |
| H01L 51/00 | (2006.01) |
| H01G 9/20 | (2006.01) |

(52) U.S. Cl.
CPC ............ *C07D 409/04* (2013.01); *C07D 405/04* (2013.01); *C07D 495/04* (2013.01); *C07D 495/14* (2013.01); *H01G 9/2059* (2013.01); *H01L 51/0086* (2013.01); *H01G 9/2031* (2013.01); *Y02E 10/542* (2013.01); *Y02E 10/549* (2013.01)

(58) Field of Classification Search
None
See application file for complete search history.

(56) References Cited

U.S. PATENT DOCUMENTS

| 6,437,130 | B1 * | 8/2002 | Paidi et al. ......................... 546/8 |
| 2005/0139257 | A1 | 6/2005 | Islam |
| 2009/0107552 | A1 | 4/2009 | Minns |
| 2009/0209762 | A1 * | 8/2009 | Wu et al. .............. C07F 15/0053 546/12 |
| 2010/0101643 | A1 * | 4/2010 | Takahashi et al. ............ 136/256 |
| 2012/0253043 | A1 * | 10/2012 | Nazeeruddin et al. ........... 546/2 |

FOREIGN PATENT DOCUMENTS

| EP | 2053618 A1 | 4/2009 |
| JP | 2004296170 A | 10/2004 |
| WO | WO 2007/046452 A1 * | 4/2007 |
| WO | 2008120810 A1 | 10/2008 |
| WO | WO 2008/120810 A1 * | 10/2008 |

OTHER PUBLICATIONS

Carey, FA. Organic Chemistry 6th Ed. McGraw Hill. 2006, chapter 1, p. 9.*
Angelis, FD. et al. Influence of the Sensitizer Adsorption Mode on the Open-Circuit Potential of Dye-Sensitized Solar Cells. Nano Letters. 2007, vol. 7, p. 3190.*
Abbotto, A. et al. Electron-rich heteroaromatic conjugated bipyridine based ruthenium sensitizer for efficient dye-sensitized solar cells. Chem. Comm. 2008, p. 5318.*
Barni, E. et al. Synthesis and photophysical characterization of highly luminescent complexes of Ru(II) containing 4,4'-di-(p-carboxyphenyl)-2,2'-bipyridine. Inorganica Chimica Acta. 1992, p. 831-839.*
Barni, E. et al. Synthesis and photophysical characterization of highly luminescent complexes of Ru(II) containing 4,4'-di-(p-carboxyphenyl)-2,2'-bipyridine. Inorganica Chimica Acta. 1992, p. 831.*
Schott, E. et al. Substituents Effects on Two Related Families of Dyes for Dye Sensitized Solar Cells [Ru(4,4'-R,R-2,2'-bpy)3]2+ and [Ru(4,4'-COOH-2,2'-bpy)(4,4'-R,R-2,2'-bpy)2]2+. The Journal of Physical Chemistry. 2012, vol. 116, p. 7436.*

(Continued)

*Primary Examiner* — Janet L Andres
*Assistant Examiner* — Ben S Michelson
(74) *Attorney, Agent, or Firm* — Taft Stettinius & Hollister LLP

(57) ABSTRACT

The present invention provides new bi- and polypyridine ligands of ruthenium dyes. The invention also provides solar cells, in particular dye-sensitized solar cells comprising the dyes. Formula(I):

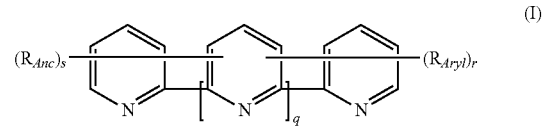

7 Claims, 12 Drawing Sheets

(56) References Cited

OTHER PUBLICATIONS

Torres, T. et al. Effect of bulky groups in ruthenium heteroleptic sensitizers on dye sensitized solar cell performance. Chemical Science. 2012, vol. 3, p. 1177.*
International Search Report; PCT/IB2010/054399.
De Angelis et al.; Influence of the Sensitizer Adsorption Mode on the Open-Circuit Potential of Dye-Sensitized Solar Cells; Nano Letter 2007, vol. 7, No. 10, pp. 3189-3195.
Abbotto et al.; Electron-rich Heteroaromatic Conjugated Bipyridine Based Ruthenium Sensitizer for Efficient Dye-Sensitized Solar Cells; Chem. Communication 2008, pp. 5318-5320.
Nazeeruddin et al.; Combined Experimental and DFT-TDDFT Computational Study of Photoelectrochemical Cell Ruthenium Sensitizers; American Chemical Society, 2005, pp. 16835-16847.
Gratzel, Michael; Photoelectrochemical Cells; Insight Review Articles, Institute of Photonics and Interfaces, Nature, vol. 414, Nov. 15, 2001.
Moore; Molecular Design of Thin Film Optoelectronic Materials for Solar Cells; JACS Editorial; 2008 American Chemical Society, 130, pp. 12201-12203.
Nazeeruddin et al.; Conversion of Light to Electricity by . . . ; 1993 American Chemical Society; pp. 6382-6390.
Renouard T. et al.; Functionalized Tetradentate Ligands for Ru-sensitized Solar Cells; Tetrahedron, Elsevier Science Publishers, Amsterdam; Aug. 2, 2001; pp. 1-6; XP004319723.
Houarner-Rassin et al.; Synthesis and Photoelectrochemical Properties of Ruthenium Bisterpyridine Sensitizers Functionalized with a Thienyl Phosphonic Acid Moiety; Journal of Photochemistry and Photobiology A: Chemistry 192, Elsevier Dequoia, Lausanne, CH; May 5, 2007; pp. 56-65; XP022307062.
Constable et al.; Hairpin Helicates: A Missing Link Between Double-Helicates and Trefoil Knots; Dalton Transactions, vol. 7; Feb. 22, 2005; pp. 1168-1175; XP002623371.
Gunther et al.; The New and Simple 'Lego' System: Synthesis and Reactioins of Thienyl-Substituted 4-tributylstannyl-2,6-oligopyridines; Tetrahedron, vol. 55; May 21, 1999; pp. 5047-5066; XP002623372.
Jacoby, Mitch; Molecular-Beam Methods and Novel Electrodes Simplify Analysis of Mixtures; Separations Science; Chem. Eng. News; Apr. 16, 2007; vol. 85, No. 16; pp. 17-21.
Beley et al.; New Ruthenium Bisterpyridinyl Complexes, as Efficient Sensitizers of Nancrystalline, TiO2 Films; Inorganica Chimica Acta, vol. 318, 201; Feb. 28, 2001; pp. 197-200, XP002580137.
Polo A.S. et al.; Metal Complex Sensitizers in Dye-Sensitized Solar Cells; Coordination Chemistry Reviews, Elsevier Science, Amsterdam; Jun. 25, 2004; pp. 1343-1361; XP004578924.
Nazeeruddin M.K., et al.; Engineering of Efficient Panchromatic Sensitizers for Nanocrystalline TiO2-Based Solar Cells, Journal of the American Chemical Society, NY; Feb. 3, 2001; pp. 1613-1624; XP001009935.
Choi et al.; Synthesis of DNA Triangles with Vertexes of Bis(terpyridine) iron (II) Complexes, J. Am Chem. Soc., vol. 126, No. 28; 2004; pp. 8606-8607; XP002623366.
Reza-Ali Fallahpour; Carboxylate Derivatives of Oligopyridines; Synthesis, No. 8; 2000; pp. 1138-1142; XP002623367.
Barolo et al.; Synthesis, Characterization, and DFT-TDDFT Computational Study of a Ruthenium Complex Containing a Functionalized Tetradentate Ligand; Inorganic Chemistry, vol. 45, No. 12; 2006; pp. 4642-4653; XP002623368.
Renouard et al.; Novel Ruthenium Sensitizers Containing Functionalized Hybrid Tetradentate Ligands: Synthesis, Characterization, and INDO/S Analysis; Inorganic Chemistry, vol. 41, No. 2; Mar. 1, 2002; pp. 367-378; XP002623369.

* cited by examiner

US 9,359,334 B2

LIGANDS FOR SENSITIZING DYES OF DYE-SENSITIZED SOLAR CELLS

This application claims the benefits under 35 U.S.C. 119 (a)-(d) or (b), or 365(b) of International Application No. PCT/IB2010/054399 filed 29 Sep. 2010, and European Patent Application No. 09171711.6, filed 29 Sep. 2009.

FIELD OF THE INVENTION

The present invention relates to new bi- and polypyridine compounds, to novel sensitizing dyes comprising the compounds as ligands, and to photoelectrical conversion devices comprising the ligands and/or the dyes.

TECHNICAL BACKGROUND AND PROBLEMS ADDRESSED BY THE PRESENT INVENTION

The need of reliable and economically viable alternative and renewable energy sources has boosted research on new materials for unconventional photovoltaics (Moore, J. S. *J. Am. Chem. Soc.*, 2008, 130, 12201, *JACS* Select special issue; Jacoby, M. *Chem. Eng. News* 2007, 85, 16). In the field of molecular-based photovoltaic devices, dye-sensitized solar cells (DSCs) have reached the best efficiencies, approaching those exhibited by conventional systems such as amorphous silicon solar modules. In addition, they show the best potential and promise for high-conversion low-cost devices (O'Regan, B.; Graetzel, M. *Nature* 1991, 353, 737; Graetzel, M. *Nature* 2001, 414, 338).

In DSCs semiconductor (for example, $TiO_2$) nanoparticles are coated with light-harvesting sensitizer dyes and are typically surrounded by a charge transporting medium, for example a liquid-phase electrolyte or an organic electron or hole transporting material. The dye-sensitizer captures photons and an electron/hole pair is generated and transferred at the interface with the inorganic semiconductor and, for example, the redox electrolyte. The photosensitizer dye is the first device interface to the external input and thus represents one of the strategic components of these cells. Ru(II)-polypyridyl dyes (Polo, A. S.; Itokazu, M. K.; Murakami Iha, N. Y. *Coord. Chem. Rev.* 2004, 248, 1343) yielding power conversion efficiencies of ca. 9-11% under standard AM 1.5 conditions, have best performed so far (Nazeeruddin, M. K.; DeAngelis, F.; Fantacci, S.; Selloni, A.; Viscardi, G.; Liska, P.; Ito, S.; Takeru, B.; Graetzel, M. *J. Am. Chem. Soc.* 2005, 127, 16835). The most representative dye of this series is the homoleptic complex bis(2,2'-bipyridyl-4,4'-dicarboxylate) ruthenium(II), carrying 4 (N3) (Nazeeruddin, M. K.; Kay, A.; Rodicio, I.; Humphry-Baker, R.; Mueller, E.; Liska, P.; Vlachopoulos, N.; Graetzel, M. *J. Amer. Chem. Soc.* 1993, 115, 6382) or 2 (N719) (Nazeeruddin, M. K.; DeAngelis, F.; Fantacci, S.; Selloni, A.; Viscardi, G.; Liska, P.; Ito, S.; Takeru, B.; Graetzel, M. *J. Am. Chem. Soc.* 2005, 127, 16835) protonated carboxylic anchoring groups to $TiO_2$.

The present inventors believe that one of the disadvantages of the currently existing dyes is the mismatch between the dye absorption band, limited to the UV-Vis region, and the solar emission, which spans to the lower energy portion of the spectrum. Therefore, it would be advantageous to design new metal complex sensitizers having a panchromatic response with improved molar extinction coefficients.

The inventors are also aware that polypyridines other than bi-pyridines have been only rarely investigated, although a series of ruthenium(II) sensitizers derived from carboxylated terpyridyl complexes of tris-thiocyanato Ru(II) (black dye) have exceeded 10% efficiencies (Pechy, P.; Renouard, T.; Zakeeruddin, S. M.; Humphry-Baker, R.; Comte, P.; Liska, P.; Cevey, L.; Costa, E.; Shklover, V.; Spiccia, L.; Deacon, G. B.; Bignozzi, C. A.; Gratzel, M. *J. Am. Chem. Soc.* 2001, 123, 1613).

Abbotto, A.; Barolo, C.; Bellotto, L.; Angelis, F. D.; Gratzel, M.; Manfredi, N.; Marinzi, C.; Fantacci, S.; Yum, J.-H.; Nazeeruddin, M. K. *Chem. Commun.* 2008, 42, 5318 have used a heteroaromatic donor 3,4-ethylenedioxythiophene ring as a substituent in a bpy ancillary ligand; such ligand was used in a Ru(II) sensitizer named Ru-EDOT, which was endowed with high photocurrent and overall conversion efficiency.

The present inventors observed, however, that heteroleptic sensitizers with anchoring sites localized on the same bipyridine ligand give rise to a decrease of the open circuit potential because of the different sensitizer adsorption mode onto $TiO_2$ compared to homoleptic sensitizers (De Angelis, F.; Fantacci, S.; Selloni, A.; Graetzel, M.; Nazeeruddin, M. K. *Nano Lett.* 2007, 7, 3189).

The inventors as well as other researchers have verified this behavior for a rather large series of heteroleptic Ru(II)-dyes; as a consequence, despite delivering increased photocurrents compared to the prototypical N3/N719 dyes, heteroleptic Ru(II)-dyes have so far not provided increased performances when employed in DSCs employing a liquid $I-/I_3-$-electrolyte.

The present invention addresses the problems set out above. More specifically, the present invention addresses the problem of providing new sensitizing dyes, which preferably absorb light in the lower energy portion of the spectrum.

It is in particular an objective of the invention to overcome the disadvantages encountered with heteroleptic dyes currently known. For example, it is an objective to provide the advantages of a heteroleptic dye such as the enhanced optical properties and photocurrents while at the same time retain a high open circuit potential or to even increase the open circuit potential.

It is thus an objective of the invention to provide sensitizing dyes that increase the overall power conversion efficiency of dye-sensitized solar cells, if compared to dyes currently available.

SUMMARY OF THE INVENTION

The present invention relates to bi- and polypyridine compounds that can be used as ligands of sensitizing dyes, which comprise at least one anchoring group and, in addition, at least one group comprising an aryl. Remarkably, the ligands achieve high absorption by way of an improved molar extinction coefficient and at the same time avoid the problem of reduced open circuit potential. The ligands may be provided, for example, in the form of a bi-pyridine ligand, which may be combined with a typical bi-pyridine anchoring ligand in a sensitizing dye. In this way, dyes comprising a total three anchoring groups may be provided. Furthermore, the ligands of the invention may be provided in the form of a tetrapyridine comprising one or more substituents for anchoring the dye to a semiconductor surface and, in addition, substituents, which increase the optical properties of the dye. The inventors were thus surprisingly able to combine the panchromatic response of tetrapyridine ligands with the superior optical properties of π-donor conjugated bipyridines.

Accordingly, the present invention provides, in a first aspect a bi- or polypyridine compound comprising a structure of formula (I):

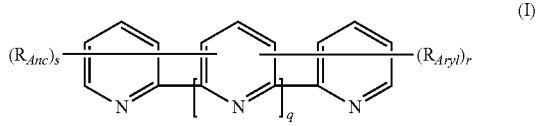

wherein $R_{Anc}$ is a substituent comprising an anchoring group (-Anc) and any one of the s substituents $R_{Anc}$ may be provided on any one of the pyridine rings of formula (I);
wherein $R_{Aryl}$ is a hydrocarbon substituent comprising from 2-60 carbons and from 0-30 heteroatoms, wherein the hydrocarbon comprises at least one aryl comprising an aromatic ring and wherein any one of the r substituents $R_{Aryl}$ may be provided on any one of the pyridine rings of formula (I);
wherein said aryl is or is not further substituted;
wherein q is selected from 0, 1, and 2;
wherein r is the number of total substituents $R_{Aryl}$ in compound (I) and is an integer of 1 to (7+(q×3));
wherein s is the number of total substituents $R_{Anc}$ in compound (I) and is an integer of 1 to (7+(q×3));
with the proviso that r+s is not greater than 8+(3×q) (× being the sign for multiplication of the indicated variables);
wherein any pyridine of the structure of formula (I) may or may not be further substituted.

Preferably, $R_{Aryl}$ and/or $R_{Anc}$ is in a π-conjugated relationship with the basic pyridine structure to which it is attached.

If the aryl comprises a ring having only 2, 3, 4 or 5 ring carbons, there are as many heteroatoms as necessary for providing a ring or ring system with aromatic properties.

In a second aspect, the present invention provides the use of the bi- or polypyridine compounds of the invention as a ligand in an organometallic compound. In particular, the present invention provides the use of the compounds of the invention as a ligand in a dye, in particular a sensitizing dye. The organometallic compounds and/or dyes may be used as sensitizers in a dye-sensitized solar cell.

In a third aspect, the present invention provides an organometallic compound comprising a formula selected from formula (X) and (XI) below:

wherein M is a metal selected from iron, ruthenium, osmium, cobalt, rhodium, iridium, nickel, palladium and platinum;
wherein $L_1$ is a bipyridine ligand according to the invention, in which q is 0;
wherein $L_2$ is selected from a bipyridine ligand according to the invention, in which q is 0, and from a bi-pyridine ligand of formula (XX) below;
wherein $L_3$ and $L_4$ are monodentate ligands;
wherein $L_5$ is a quaterpyridine ligand according to the invention, in which q is 2;

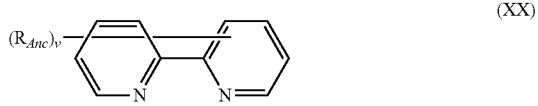

wherein said bi-pyridine ligand of formula (XX) comprises at least one anchoring ligand $R_{Anc}$ as defined herein; and wherein the bi-pyridine structure (XX) is or is not further substituted, and wherein v is 1, 2, 3, or 4, preferably 2.

In further aspects, the present invention generally provides dyes comprising the bi- and/or polypyridine compounds of the invention and dye-sensitized solar cells comprising the dyes and/or the compounds.

In still further aspects, the present invention provides photoelectrochemical devices, photoelectric conversion devices, photovoltaic devices and/or solar cells comprising the bi- or polypyridine compound of the invention and/or the organometallic compounds of the present invention.

BRIEF DESCRIPTION OF THE DRAWINGS

In the figures,
FIG. 1b shows the synthesis of the dye (7) in greater detail.

DETAILED DESCRIPTION OF THE PREFERRED EMBODIMENTS

Figure 1A:
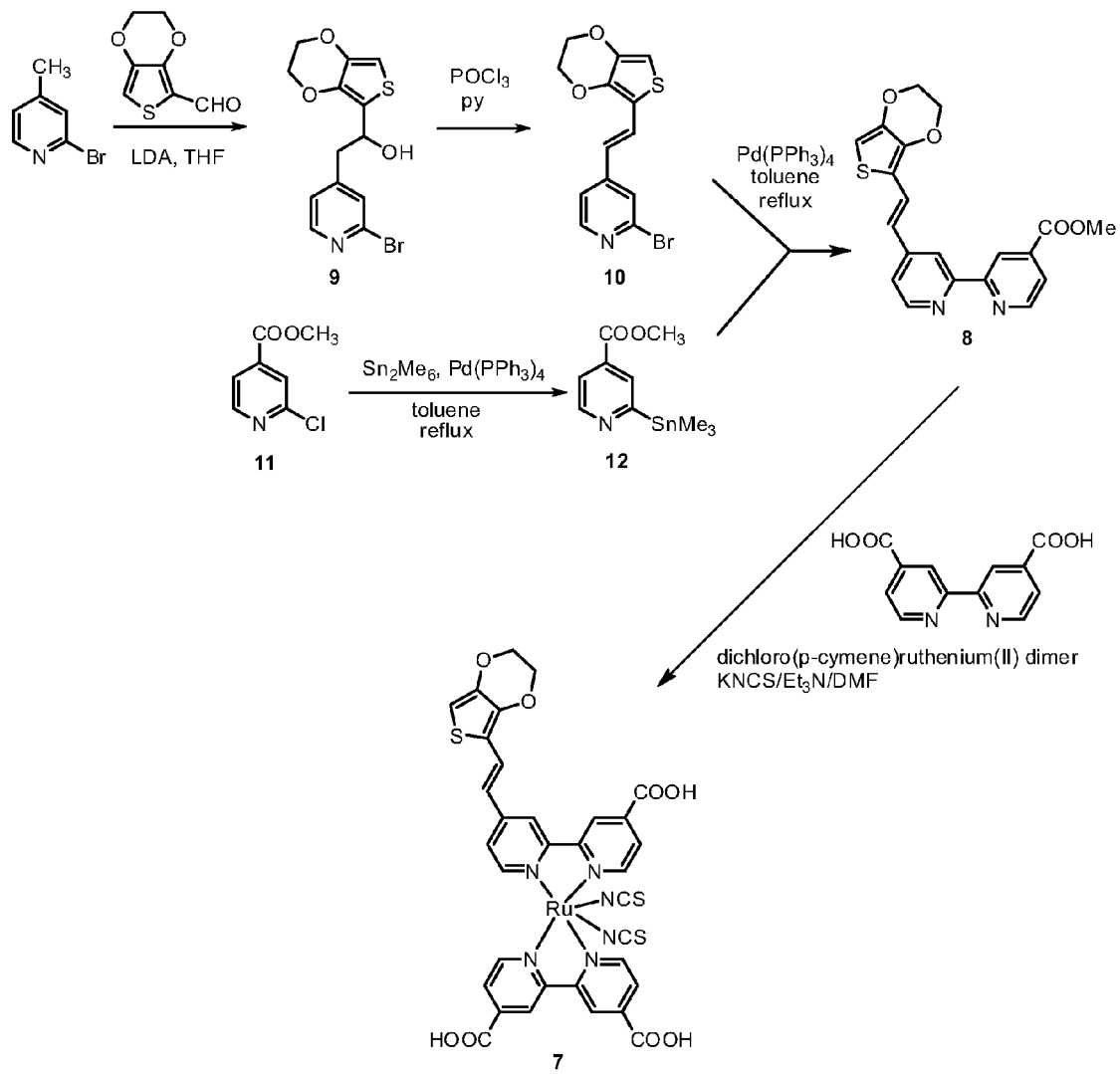
FIGS. 1a and 1b show schemes of the synthesis of a bipyridine ligand according to the invention and of a heteroleptic dye (compound 7) comprising the ligand, also according to the invention. Compound 8 shown in FIG. 1a is the precursor of the ligand of the invention, the final ligand being obtained by the hydrolysis of the methyl ester to COOH, as is done in the synthesis of compound 7.

The present invention provides compounds of formula (I) as defined above. In these compounds, q is preferably selected from 0, 1 and 2. If q is 0, the compound of the invention comprises a substituted bi-pyridine structure. If q is 1, the compound is a terpyridine, and if q is 2, the compound is a quaterpyridine. For the purpose of the present specification, ter- and quaterpyridines are considered to be polypyridines.

The term "comprising" or "comprises", for the purpose of the present specification, is intended to mean "includes, amongst other". It is not intended to mean "consists only of".

The bi- or polypyridine compounds of the invention comprise one or more (s) substituents $R_{Anc}$ and one or more (r) substituents $R_{Aryl}$. The substituents $R_{Anc}$ and $R_{Aryl}$ are structurally different. In particular, the substituent $R_{Aryl}$ lacks a functional anchoring group as provided on substituent $R_{Anc}$. The definition of an anchoring group is provided further below. This does not preclude the possibility of $R_{Aryl}$ to comprise a functional group comprising the structure of an anchoring group as defined herein below but being chemically modified or arranged in a way that it cannot function as an anchoring group.

In the bi- or polypyridine compounds of the invention the substituents $R_{Anc}$ and/or $R_{Aryl}$ may be provided on any one of the pyridine rings comprised in the overall bi- or polypyridine structure. Each pyridine ring may or may not be substituted, independently from any other pyridine ring. In the compound of the invention there is at least one substituent $R_{Anc}$ and at least one substituent $R_{Aryl}$.

For example, the compound may comprise one substituent $R_{Aryl}$ and one substituent $R_{Anc}$. According to further embodiments of the invention, the compound of formula (I) may comprise one substituent $R_{Aryl}$ and two substituents $R_{Anc}$, two substituents $R_{Aryl}$ and one substituent $R_{Anc}$, two substituent $R_{Aryl}$ and two substituents $R_{Anc}$, three substituents $R_{Anc}$ and one substituent $R_{Aryl}$, and so forth, just to mention a few possibilities. If there are more than one substituent of a category (that is, more than one substituent $R_{Aryl}$ and/or more than one substituents $R_{Anc}$) each substituent of the same category may be the same or different from the other substituent(s) of the same category.

According to a preferred embodiment, in the compound of formula (I), r and s independently are an integer of 1 to (3+(q×2)), more preferably 1 to (2+(q×2)), and most preferably 1 to (1+(q×2)) (which means that r and/or s are 1, if q is 0).

According to a preferred embodiment, the sum of r+s is not larger than (6+(q×3)), preferably not larger than (6+(q×2)), more preferably not larger than (4+(q×2)). For example, r+s is preferably (2+(q×2)).

The substituents $R_{Anc}$ and/or $R_{Aryl}$ may be provided on the same pyridine ring. The compound of the invention may independently comprise more than one of each of the substituents $R_{Aryl}$ and $R_{Anc}$, respectively. Preferably they are provided on separate pyridine rings. The designation "Anc" indicates that the respective substituent $R_{Anc}$ comprises an anchoring group, suitable to anchor the entire compound to a substrate of interest. Preferred exemplary substrates and anchoring groups are disclosed further below. The designation "Aryl" indicates that the respective substituent $R_{Aryl}$ comprises at least one aromatic ring. According to an embodiment, at least one aromatic ring comprises at least one heteroatom selected from O, S, NR (with R being, for example, an alkyl or aryl as defined below), and Se in the ring.

Besides the substituents $R_{Anc}$ and $R_{Aryl}$, the bi- and polypyridine compounds of the invention may be further substituted.

Further substituents of the bi- or polypyridine structure of formula (I) may be selected from halogen (in particular F, Cl, Br, I, preferably F, Cl and Br), functional groups that are free of any carbon atom, in particular hydroxyl (—OH), and —NO$_2$, —NH$_2$, and from hydrocarbons comprising from 1-30 carbons and from 0-10 heteroatoms, preferably 1-25, more preferably 1-20, and most preferably 1-10 carbons and 1-5 heteroatoms.

Heteroatoms, for the purpose of the present specification, include in particular halogens and the atoms O, S, Se, N, P, As, but possibly also metals and metalloids (B, Si, etc.). Preferably, heteroatoms are selected from O, S, N, P and from halogen. More preferably, heteroatoms are selected from O, S, N, F, Cl, I, Br.

Examples of hydrocarbons that provide the optional further substituents on the bi- or polyperidine structure may be selected from alkyls, alkenyls, alkynyls, acyls and aryls, said alkyls, alkenyls, alkynyls and acyls may be linear, branched or cyclic, and wherein said alkyls, alkenyls, alkynyls, acyls and aryls may or may not be further substituted an may comprise one or more heteroatoms. The heteroatoms may, for example, replace a carbon and/or may be provided in the form of a functional group. The alkyls, alkenyls, alkynyls, acyls and aryls may, for example, be partially or totally halogenated.

For example, the hydrocarbon may comprise a hydrocarbon chain, branched, cyclic and/or polycyclic structure, in which one or more carbon atoms are replaced by heteroatoms, in particular O, N, S. Furthermore, the hydrocarbon may comprise further donor/acceptor functional groups. Non-limitative examples of such functional groups are —NO$_2$, —NH$_2$, carbonyl and carboxylic functionalities, phosphates and other functionalties including P and double bonds.

According to a preferred embodiment, further substituents are selected from: halogen, hydroxyl (—OH), cyano (—C≡N), —NO$_2$, C1-C25 alkyl, C2-C25 alkenyl, C2-C25 alkynyl, C2-C25 aryl, C1-C25 alkoxyl, C1-C25 acyl, C2-C10 ether (other than alkoxyl) and C2-C25 polyether (including alkoxyls), wherein alkyl, alkenyl, alkynyl, alkoxyl, acyl, ether, polyether and said aryl may or may not still be further substituted, for example by halogen, —OH, alkyl and alkenyl; and wherein said further substituents may further be selected from: amino groups of the formula —NH$_2$, NHR, and/or —NRR', wherein any R and R' may be the same or different and be selected from the alkyl, alkenyl, alkynyl, aryl and ether as defined above, and from amino groups of the formula —R$_M$—NH$_2$, —R$_M$—NHR, and —R$_M$—NRR' wherein any R and R' is independently as defined above and —R$_M$— is selected from a C1-C25 alk-diyl (for example methylene), C2-C25 alken-diyl, C2-C25 alkyn-diyl, C2-C25 ar-diyl (for example phenylene), C1-C25 alkoxy-diyl (for example methox-1-yl, C1-C25 acyl, C2-C25 ether (other than alkoxyl) and C2-C25 polyether (including alkoxyls), with the proviso that the atom of $R_M$, which is covalently bound to the nitrogen atom, is a carbon; and wherein said further substituents may further be selected from: hydroxyalkyl (for example $-(CH_2)_u-OH$), alkylalkoxy (for example $-(CH_2)_u-OR$), carboxylic derivatives other than $R_{Anc}$, functionalities containing S and P, for example $-S(O)_2OR$, $-S(O)_tR$, $-P(O)(OR)(OR')$, wherein $u$ is an integer from 1-25, preferably 1-10, wherein t is 0, 1, or 2, and R and R' are independently as defined above.

Since the term aryl encompasses heteroaryls it is clear that if the aryl has only 2, 3, 4 and 5 carbon atoms, the aromatic ring comprises sufficient heteroatoms so as to provide a ring having aromatic properties. For example, aryls with two carbon atoms are triazole radicals and benzothiodiazole radicals.

Examples of carboxylic derivatives other than $R_{Anc}$ include, for example, alkyl carboxylate (alkyloxycarbonyl), alkenyl carboxylate (alkenyloxycarbonyl), alkynyl carboxylate (alkynyloxycarbonyl), aryl carboxylate (aryloxycarbonyl), wherein said alkyl, alkenyl, alkynyl and aryl are as defined above.

According to a still more preferred embodiment, further substituents are selected from halogen, hydroxyl (—OH), alkyl, alkenyl, alkynyl, aryl, hydroxyalkyl (for example $-(CH_2)_u-OH$), alkoxy (—O—R), alkylalkoxy (for example $-(CH_2)_u-OR$), amino (—NH$_2$, NHR, and/or —NRR'), alkylamino, (for example $-(CH_2)_u-NH_2$, $-(CH_2)_u-NHR$, and $-(CH_2)_u-NRR'$), cyano, (—CN), carbonyl (—COR), carboxylic derivatives other than $R_{Anc}$, functionalities containing S and P, for example $-S(O)_2OR$, $-S(O)_tR$, $-P(O)(OR)(OR')$, wherein u, t, R and R' are defined as above, and from other hydrocarbons comprising from 1-25 carbons and from 0-10 heteroatoms.

According to an embodiment, further substituents comprise independently up to 25, up to 20, up to 15, up to 10, up to 8, up to 6, and most preferably up to 4 carbons. These preferred numbers of carbon atoms apply independently to all kind of further substituents defined herein (alkyl, alkenyl, alkynyl, aryl, amino, etc.)

Further substituents are preferably attached to a carbon atom of the structure carrying the further substituent (such as, for example, the structures of formula (I), (IV), (V), (XX), (XXI) and/or the moieties $A_Z$ and $B_X$ hereinbelow).

According to a preferred embodiment, the bi- or polypyridine structure is not further substituted besides the substituents $R_{Anc}$ and $R_{Aryl}$.

According to an embodiment of the compound of the invention, the substituent —$R_{Aryl}$ comprises from 2-40 carbons and from 1-20 heteroatoms and comprises at least one heteroaryl comprising an aromatic ring with at least one heteroatom selected from O, S and Se; wherein said heteroaryl is or is not further substituted. Preferably, said aromatic ring is in a π-conjugated relationship with the basic bi- or polypyridine structure, for example the one of formula (I).

According to an embodiment of the compound of the invention, $R_{Anc}$ is a substituent of formula (II) below:

(II)

wherein n is 0 or an integer of 1-5, and Z, if present (n≥1) is an integer of the group of integers 1, ..., n, wherein any $A_Z$ represents the $Z^{th}$ moiety of the n successive moieties $A_1$- ... -$A_n$, wherein any $A_Z$ may be different from any other $A_Z$; wherein any moiety $A_Z$ is independently selected from an aryl, vinylene (—=—) and ethyne-diyl (—≡—), said $A_Z$ being, if it is an aryl or a vinylene, besides the substituent Anc (if applicable), independently further substituted or not further substituted, and said aryl comprising from 2-50, preferably 3-40, more preferably 4-35, carbon atoms and 0-15, preferably 0-10, more preferably 1-15 and most preferably 1-10 heteroatoms; and, wherein Anc is the anchoring group.

Preferably, $A_1$ is in a π-conjugated relationship with the basic bi- or polypyridine structure (in particular of formula (I), (IV), (V), (XX) and (XXI), respectively). Even more preferably, all successive $A_Z$ moieties are in a π-conjugated relationship with their respective preceding neighbouring $A_Z$ moiety, and preferably with the basic bi- or polypyridine basic structure to which $R_{Anc}$ is attached.

As mentioned, any moiety $A_Z$ (if it is aryl or vinylene) may be further substituted. With respect to further substituents, the same as mentioned above with respect to the possible further substituents on the bi- or polypyridine structure applies independently. Preferred further substituents of $A_Z$ are in particular independently selected from the further substituents according to the preferred and more preferred embodiments as defined above. Preferably, further substituents are attached to a carbon atom of $A_Z$.

For example, if n is 3, the substituent $R_{Anc}$ according to formula (II) is a substituent of formula -$A_1$-$A_2$-$A_3$-Anc, wherein anyone of $A_1$, $A_2$ and $A_3$ is independently selected.

According to a preferred embodiment, n is independently selected from 0, 1, 2 and 3, preferably is independently selected from 0, 1 or 2, most preferably n is 2.

According to an embodiment of the compound of the invention, the substituent $R_{Aryl}$ is a substituent of formula (III) below:

(III)

wherein m is an integer of 1-10, and X is an integer of the group of integers 1, ..., m, wherein any $B_X$ represents the $X^{th}$ moiety of the m successive moieties $B_1$- ... -$B_m$, wherein any $B_X$ may be different from any other $B_X$; wherein any moiety $B_X$ is independently selected from an aryl, vinylene (—=—) and ethyne-diyl (—≡—), said $B_X$ being, if it is an aryl or a vinylene, besides the substituent $R_{16}$ (if applicable), independently further substituted or not further substituted, and said aryl and said aryl comprising from 2-50, preferably 3-40, more preferably 4-35, most preferably 4-25 carbon atoms and 0-15, preferably 0-10, more preferably 1-15 and most preferably 1-10 heteroatoms; and wherein $R_{16}$ is selected from H, and further substituents as defined above. Preferably, $R_{16}$ is selected from H, halogen, —OH and from a C1-C20 hydrocarbon comprising from 0-10 heteroatoms.

Preferably, $B_1$ is in a π-conjugated relationship with the basic bi- or polypyridine structure (in particular of formula (I), (IV), (V), (XX) and (XXI), respectively). Even more preferably, all successive $B_X$ moieties are in a π-conjugated relationship with their respective preceding neighbouring $B_X$ moiety, and preferably with the basic bi- or polypyridine basic structure to which $R_{Aryl}$ is attached.

According to an embodiment, $R_{16}$ is selected independently from the further substituents defined above.

For example, if m is 3, the substituent $R_{Aryl}$ according to formula (III) is a substituent of formula —$B_1$—$B_2$—$B_3$—$R_{16}$, wherein anyone of $B_1$, $B_2$ and $B_3$ is independently selected.

According to an embodiment, at least one moiety $B_X$ in the substituent of formula (III) is an aryl moiety.

According to an embodiment of the compound comprising a substituent —$R_{Aryl}$ of formula (III), at least one $B_X$ is selected from a heteroaryl carbon atoms as indicated above and 1-10 heteroatoms, said heteroaryl comprising an aromatic ring with at least one heteroatom selected from O, S, N and Se, and said heteroaryl being further substituted or not further substituted, besides substituent $R_{16}$ (if applicable). The words "If applicable" in brackets express the fact that $R_{16}$ is present only on the terminal $B_X$ moiety.

According to a preferred embodiment, m is selected from an integer of 1-5, preferably 1-3 and most preferably m is 1 or 2.

As mentioned, any moiety $B_X$ (if it is aryl or vinylene) may be further substituted. With respect to further substituents, the same as mentioned above with respect to the possible further substituents on the bi- or polypyridine structure applies independently. Preferred further substituents of $B_X$ are in particular selected independently from the further substituents according to the preferred and more preferred embodiments as defined above.

According to an embodiment, q is 0 and the compound of the invention comprises a structure of formula (IV):

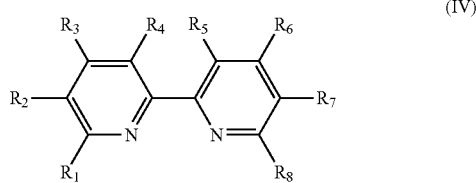

(IV)

wherein 1 to 7 substituents of the substituents $R_1$-$R_8$ is/are selected independently from a sub stituent $R_{Anc}$;
wherein 1 to 7 substituents of the substituents $R_1$-$R_8$, which is/are not a substituent $R_{Anc}$, is/are selected independently from a substituent $R_{Aryl}$; wherein any substituent of $R_1$-$R_8$, which is not a substituent $R_{Anc}$ or $R_{Aryl}$, is independently selected from H and from a further substituent as defined above, in particular from the further substituents of the preferred or more preferred embodiment as defined above. Most preferred substituents other that $R_{Anc}$ or $R_{Aryl}$, which are not H, are selected from halogen, hydroxyl (—OH), amino (—$NH_2$), and from a hydrocarbon comprising from 1-25 carbons and from 0-10 heteroatoms.

According to an embodiment of the compound of formula (IV) one of the substituents $R_1$-$R_8$ is a substituent $R_{Anc}$ and another one from $R_1$-$R_8$, which is not $R_{Anc}$, is $R_{Aryl}$.

According to a preferred embodiment of the compound of formula (IV), one of the substituents $R_1$-$R_4$ is selected from $R_{Anc}$; and one of the substituents selected from $R_5$-$R_8$ is selected from a substituent $R_{Aryl}$ as defined in this specification.

According to a preferred embodiment, $R_3$ is a substituent $R_{Aryl}$ and/or $R_6$ is a substituent $R_{Anc}$. Preferrably, the substituents $R_1$, $R_2$, $R_4$, $R_5$, $R_7$ and $R_8$ are H.

According to a preferred embodiment of the compound of formula (IV), any substituent, which is neither $R_{Anc}$ nor $R_{Aryl}$, is H.

According to an embodiment, the compound of the invention comprises a tetrapyridine structure of formula (V):

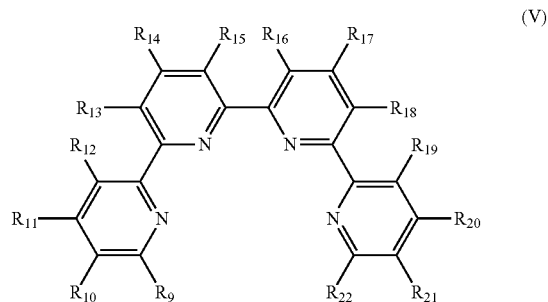

(V)

wherein 1 to 13 substituents of the substituents $R_9$-$R_{22}$ is/are selected independently from a sub stituent $R_{Anc}$;
wherein 1 to 13 substituents of the substituents $R_9$-$R_{22}$, which is/are not a substituent $R_{Anc}$, is/are selected independently from substituents $R_{Aryl}$;
wherein any substituent of $R_9$-$R_{22}$, which is not a substituent $R_{Anc}$ or $R_{Aryl}$, is independently selected from H and from a further substituent as defined above, in particular from the further substituents of the preferred or more preferred embodiment as defined above.

Most preferred substituents other that $R_{Anc}$ or $R_{Aryl}$ of the compound of formula (V), if they are not H, are selected from halogen, hydroxyl (—OH), C1-C25 alkyl, C2-C25 alkenyl, C2-C25 alkynyl, C2-C25 aryl (including heteroaryls), C1-C25 hydroxyalkyl (for example —$(CH_2)_u$—OH), C1-C25 alkoxy (—O—R), C1-C25 alkylalkoxy (for example —$(CH_2)_u$—OR), amino (—$NH_2$, NHR, and/or —NRR'), alkylamino, (for example —$(CH_2)_u$—$NH_2$, —$(CH_2)_u$—NHR, and —$(CH_2)_u$—NRR'), cyano, (—CN), carbonyl (—COR), carboxylic derivatives other than $R_{Anc}$, functionalities containing S and P, for example —$S(O)_2OR$, —$S(O)_tR$, —$P(O)(OR)(OR')$, wherein u is an integer of 1-25, preferably 1-15, t, R and R' are defined as above, and from other hydrocarbons comprising from 1-25 carbons and from 0-10 heteroatoms.

According to an embodiment of the compound of formula (V) one, two or three substituents of the substituents $R_9$-$R_{22}$ is/are a substituent $R_{Anc}$ and, independently, one, two or three substituents of the substituents $R_9$-$R_{22}$, which is (or are) not $R_{Anc}$, is/are $R_{Aryl}$.

According to an embodiment of the compound of formula (V), one or more of substituents $R_{13}$-$R_{18}$ is/are independently selected from $R_{Anc}$ and/or one or more of substituents $R_9$-$R_{12}$ and $R_{19}$-$R_{22}$ is/are independently selected from $R_{Aryl}$.

According to another embodiment, two selected from the substituents $R_{13}$-$R_{18}$ are independently selected from $R_{Anc}$ and/or one selected from substituents $R_9$-$R_{12}$ and one selected from $R_{19}$-$R_{22}$ is/are selected from $R_{Aryl}$.

According to a preferred embodiment, $R_{14}$ and $R_{17}$ are independently selected from substituents $R_{Anc}$ and/or $R_{11}$ and $R_{20}$ are independently selected from substituents $R_{Aryl}$.

According to an embodiment, the compound of formula (V) is a symmetrical compound. Accordingly, the compound comprises at least one pair of substituents $R_{Anc}$ and at least one pair of substituents $R_{Aryl}$, wherein both substituents $R_{Aryl}$ are identical and both substituents $R_{Anc}$ are identical. The characteristic of "symmetry" does not preclude that anchoring groups are differently protonated/deprotonated or provided in the form of inorganic or organic salts independently from the according situation in another, otherwise identical anchoring group. For example, if there are two —COOH anchoring groups, one of them may be protonated, the other deprotonarted, or one protonated and the other provided in the form of a tetrabutylammonium salt. Since both comprise an anchoring group derived from —COOH, the anchoring groups are considered generally identical and the compound may still be considered as symmetrical, if this difference is the only between the anchoring substituents.

All substituents which are not $R_{Anc}$ and which are not $R_{Aryl}$ in the preferred compounds of formula (IV) and (V) are defined as the further substituents as defined above, in particular with respect to the basic bi- or polypyridine structure of formula (I).

According to a preferred embodiment of the compound of formula (V), any substituent, which is neither $R_{Anc}$ nor $R_{Aryl}$, is H.

The definitions and embodiments of $R_{Aryl}$ and $R_{Anc}$ defined further above, with the preferred values of n and m apply also apply independently to the according substituents in the preferred compounds of formula (IV) and (V).

According to an embodiment of the substituents $R_{Aryl}$, any moiety $A_Z$ is independently selected from the moieties of formula (1)-(30) below:

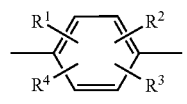
(1)

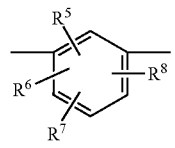
(2)

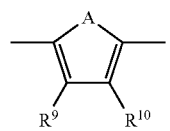
(3)

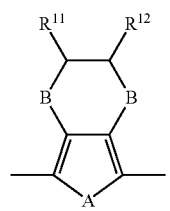
(4)

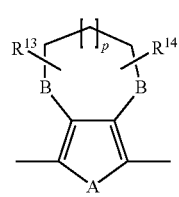
(5)

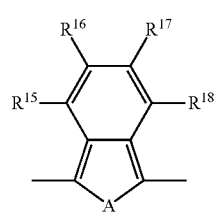
(6)

-continued

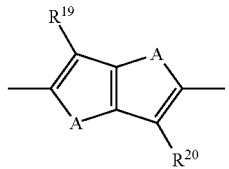
(7)

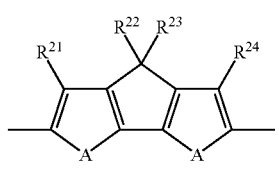
(8)

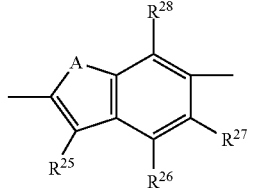
(9)

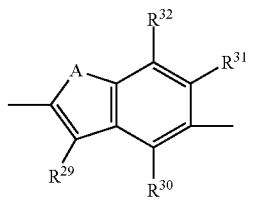
(10)

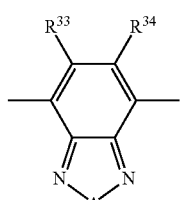
(11)

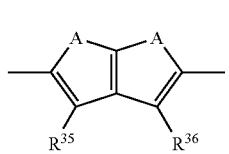
(12)

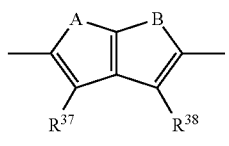
(13)

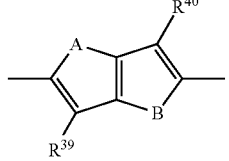
(14)

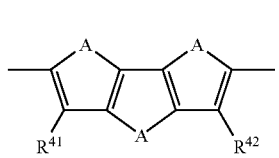
(15)

-continued
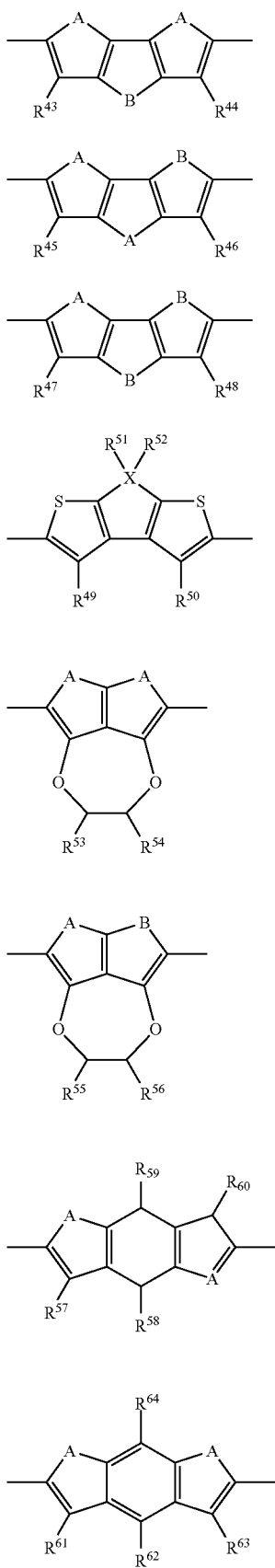
(16)
(17)
(18)
(19)
(20)
(21)
(22)
(23)
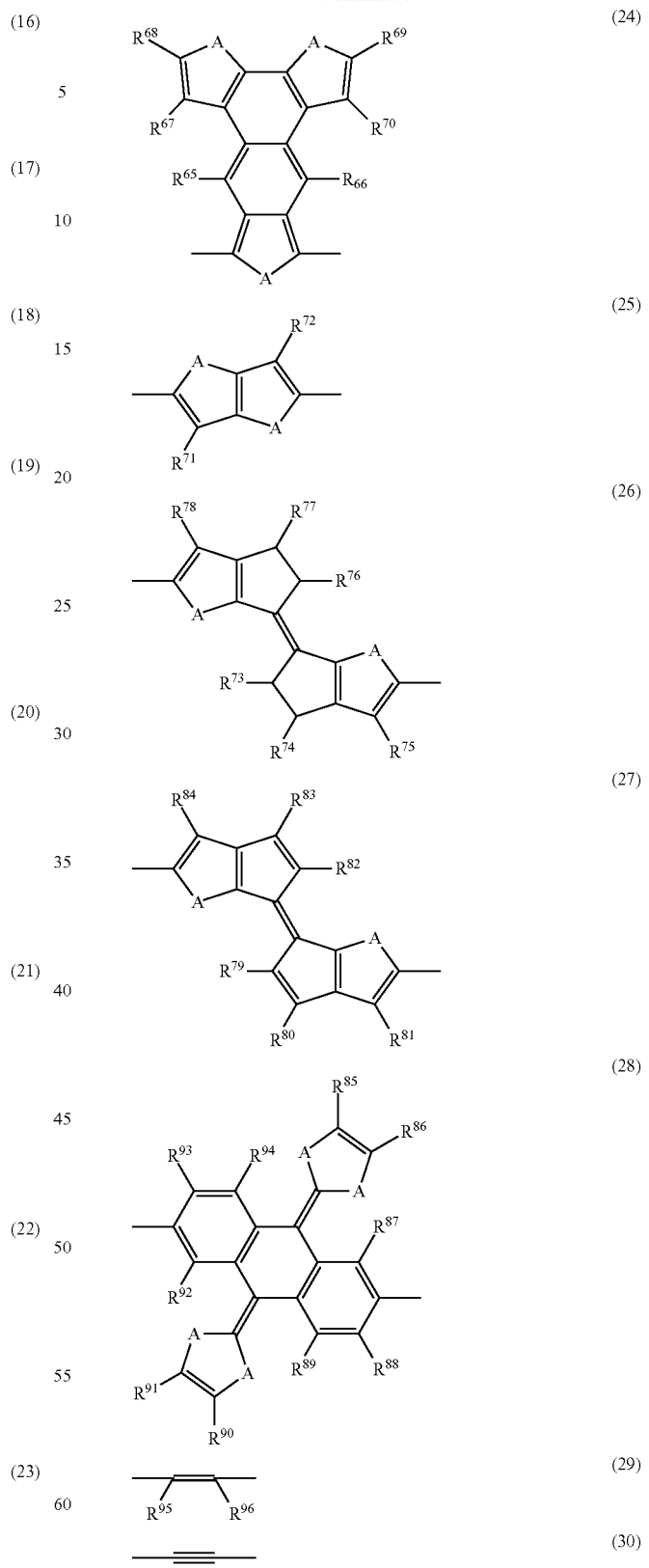
(24)
(25)
(26)
(27)
(28)
(29)
(30)
wherein A and B, if applicable, are the same or different and are a heteroatom selected from O, S, NR, and Se, with R=H, alkyl, or aryl;

wherein, in moiety (19), X is selected from any one of C, Si, Ge, Sn or Pb;

wherein, in moiety (5), p is an integer of 1-3, preferably 1-2 and wherein $R^{13}$ and $R^{14}$ may be bound to the same carbon atom;

wherein any one of $R^1$-$R^{96}$ is independently selected from H, and further substituents as defined above, in particular from H and the preferred and more preferred embodiments of the further substituents as defined above.

According to a most preferred embodiment, further substituents $R^1$-$R^{96}$ are selected from H and halogen, hydroxyl (—OH), C1-C25 alkyl, C2-C25 alkenyl, C2-C25 alkynyl, C2-C25 aryl (including heteroaryls), C1-C25 hydroxyalkyl (for example —(CH$_2$)$_u$—OH), C1-C25 alkoxy (—O—R), C1-C25 alkylalkoxy (for example —(CH$_2$)$_u$—OR), amino (—NH$_2$, NHR, and/or —NRR'), alkylamino, (for example —(CH$_2$)$_u$—NH$_2$, —(CH$_2$)$_u$—NHR, and —(CH$_2$)$_u$—NRR'), cyano, (—CN), C2-C25 carbonyl (—COR), C2-C25 carboxylic derivatives other than $R_{Auc}$, functionalities containing S and P, for example —S(O)$_2$OR, —S(O)$_t$R, —P(O)(OR)(OR'), wherein u is an integer of 1-15, t, R and R' are defined as above, and from other hydrocarbons comprising from 1-25 carbons and from 0-10 heteroatoms.

In the moieties of formula (1)-(30), the connection of any moiety to the basic structure of any one of formula (I), (IV) and/or (V), or to a preceding moiety (for example, if n is >1), is illustrated by way of a horizontal bond, which is not further specified and which is generally situated on the left side of the moieties as shown above. A similar horizontal bond is found on the right side of the moiety as depicted, indicating the connection to the anchoring group (or to $R_{16}$, where applicable), or to the following moiety, if present.

According to an embodiment, A and B in the moieties (3)-(28) are selected independently from S and O, wherein in any moiety, any A always represents the same atom (always S or always O). According to a preferred embodiment, A is S. Preferably, A is S and B is O. According to another embodiment, A and B are both S.

According to a preferred embodiment, the substituent $R_{Aryl}$ comprises at least one aryl or heteroaryl selected from the moieties of formula (1)-(28) above.

According to another embodiment, $R_{Aryl}$ comprises one or more moieties of formula (1) or (2). According to an embodiment, any one selected from $R^1$-$R^8$ of moiety (1) and (2) may be selected from H, halogen, C1-C25 alkyl, C2-C25 alkenyl, C2-C25 alkynyl; C4-C25 aryl, —Y—$R^{99}$, wherein Y may be O, S, Se or —NR$^{100}$, wherein —$R^{99}$ and —$R^{100}$ are the same or different and are independently selected from H, C1-C25 alkyl, C2-C25 alkenyl, C2-C25 alkynyl; C4-C25 aryl, wherein said alkyl, alkenyl or alkynyl may comprise one or more heteroatoms selected from O and S and wherein said C4-C25 aryl may comprise one or more ring heteroatoms selected from S, O, and N.

According to an embodiment, $R_{16}$ (of substituent of formula (III) and its embodiments) is a substituent selected from substituents as defined for for $R^1$-$R^8$ above. According to an embodiment, $R_{16}$ is selected from H, halogen, —OH, —OR (R as defined above), C1-C5 alkyl, and from C1-C5 alkoxyl.

According to an embodiment, the substituent —$R_{Aryl}$ comprises at least one heteroaryl, which is selected from the moieties of formula (3)-(28) as defined above. With respect to the substituent of formula (III), this means that at least one moiety $B_X$ is selected from the moieties of formula (3)-(28) as defined above.

According to a preferred embodiment, $R_{Aryl}$ is selected from substituents of formula (VI) and (VII) below:

$$-B_1-R_{16} \quad (VI);$$

$$-B_1-B_2-R_{16} \quad (VII);$$

wherein, in substituent (VI), $B_1$ is selected from the moieties (3), (4) and (5) above; and, wherein, in substituent (VII), $B_1$ is selected from the moieties (1), (2), (3), (4), (5), (29) and (30) above, and $B_2$ is selected from substituents (3), (4), (5), wherein, in substituents (VI) and (VII), A and B are independently as defined above, but preferably A is S and B is O; and wherein substituents of (1), (2), (3), (4), (5), (29) are independently selected from H and from the further substituents as defined above;

wherein $R_{16}$ is independently also selected from H and from further substituents as defined above.

According to a preferred embodiment, possible substituents on the moieties indicated above or on $R_{16}$ are selected from H, halogen, —OH, C1-C5 alkyl, cyano (—CN), and from C1-C5 alkoxyl.

With respect to the at least one anchoring group Anc of $R_{Anc}$, it is noted that the anchoring group is a group that is capable or susceptible of attaching and/or connecting the compound comprising the anchoring group to a surface of choice, in particular to a semiconductor material. Preferred semiconductor materials are provided below. The semiconductor materials is preferably provided in the form of a mesoscopic porous nanocristalline material. The connection to the surface of choice is preferably such that electrons can move through the compound to the surface. The connection can be electrostatic interaction and/or a covalent connection and/or coordinate covalent, which is stable for at least a 10 hours, preferably at least 10 weeks, more preferably at least 10 months and ideally up to and more than 1-3 years.

According to an embodiment, any anchoring group (Anc) is selected, independently, from any other anchoring group, from —COOH, —PO$_3$H$_2$, —PO$_4$H$_2$, —P(R$^{101}$)O$_2$H (phosphinic acid); —SO$_3$H$_2$, —CONHOH$^-$, acetylacetonate, deprotonated forms of the aforementioned, organic and/or inorganic salts of said deprotonated forms, and chelating groups with Π-conducting character;

wherein R$^{101}$ is a hydrocarbon comprising from 1 to 100 carbons and 0-50 heteroatoms, said hydrocarbon being covalently bound to the P atom of said phosphinic acid group by a carbon atom; and wherein R$^{101}$ may be further covalently connected to the bi- or polypyridine ligand carrying the anchoring group Anc.

An example of an anchoring group is acetylacetonate of formula (Anc3) below, wherein Anc3 is connected to the terminal moiety $A_n$ carrying it by a covalent bond to one selected from carbon 1, 3 or 5, preferably carbon 3, of the compound of formula (Anc3):

(Anc3)

As the skilled person appreciates, the keto and enol tautomeric forms of the anchoring group Anc3 coexist in solution, which are thus both encompassed by the present invention.

The present inventors believe that the proton of the anchoring group may have some undesired properties when adsorbed on the surface. Therefore, the inventors believe that it is advantageous if one or more of the anchoring groups are provided in a deprotonated form.

Individual deprotonated anchoring groups may be provided in the form of salts of inorganic compounds (for example metals with the charge 1+) or organic cations. A preferred organic cation in this respect is tetrabutylammonium or a substituted or unsubstituted imidazolium. Therefore, even if the compound of the invention is otherwise symmetrical, the individual anchoring groups, even if they are of the same principle nature (for example: carboxylic acid), may be differently protonated or provided as different salts. If the different cation of the anchoring group (H+, organic, inorganic), or the absence of a cation at the anchoring group is the only difference between a pair of anchoring substituents, this is not considered, for the purpose of the invention, to have an impact on the overall symmetry of the compound. While such differences may have a benefit, it is considered that it is the same general anchoring group.

Figure 3A:
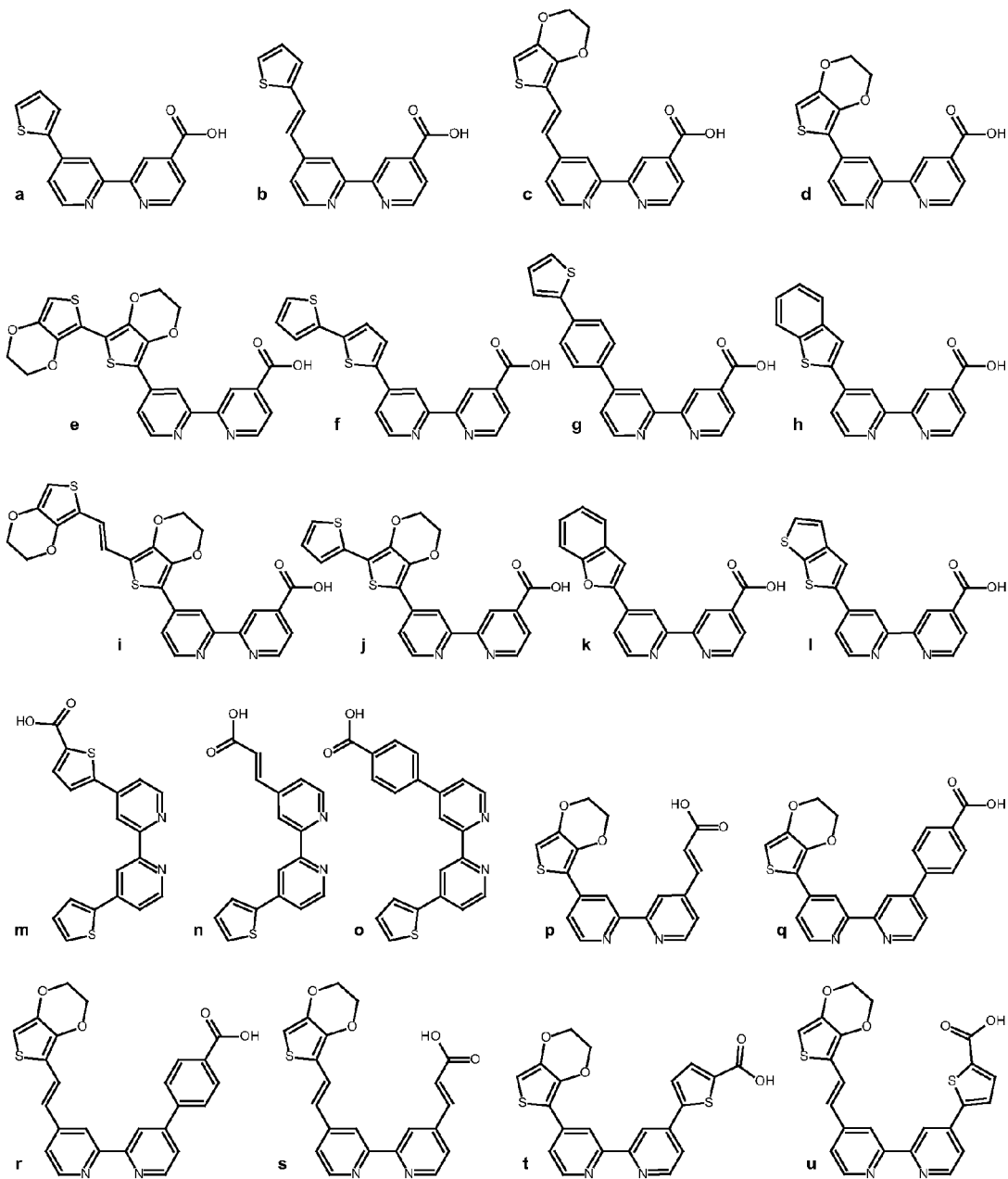
FIGS. 3a and 3b show exemplary bi-pyridine ligands a-y and a1-i1, respectively that can be used in sensitizing dyes for DSCs in accordance with the present invention.
Figure 3B:
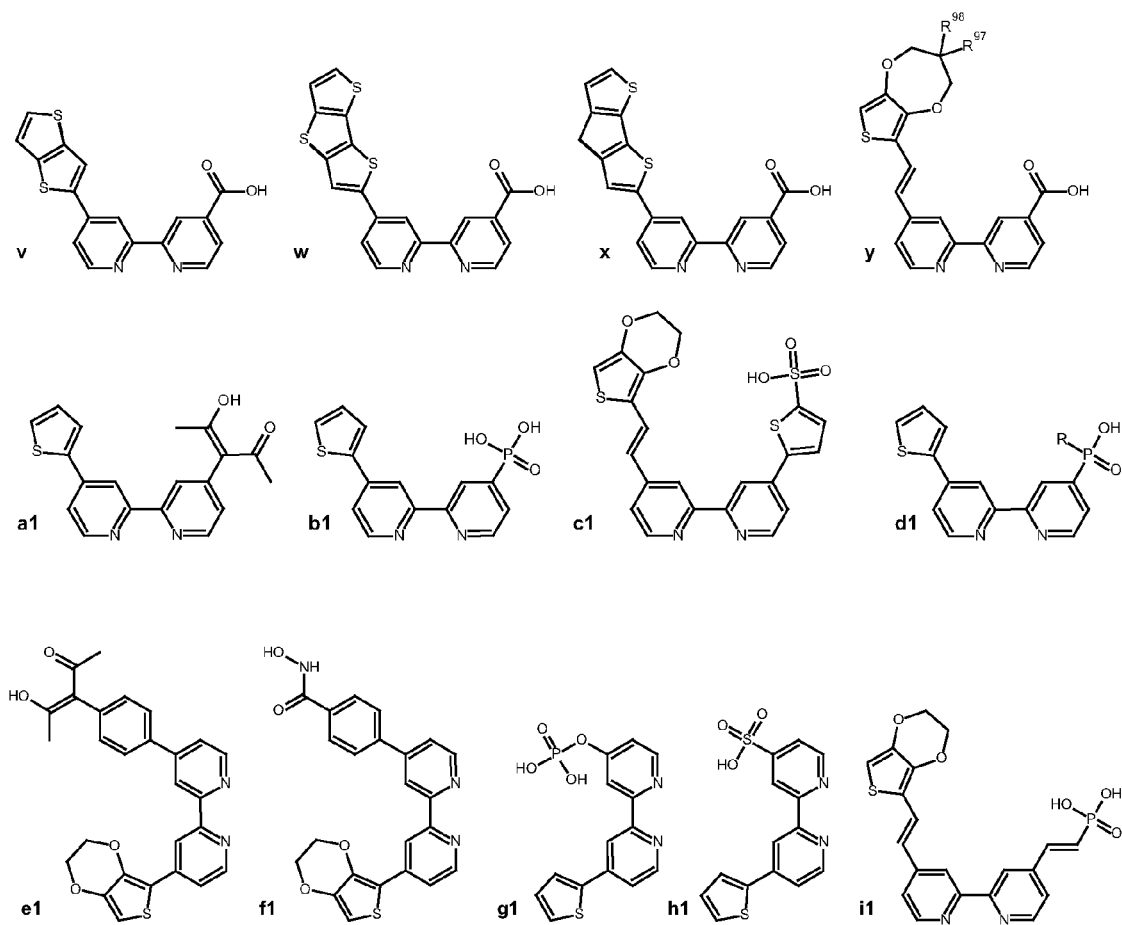
Figure 4A:
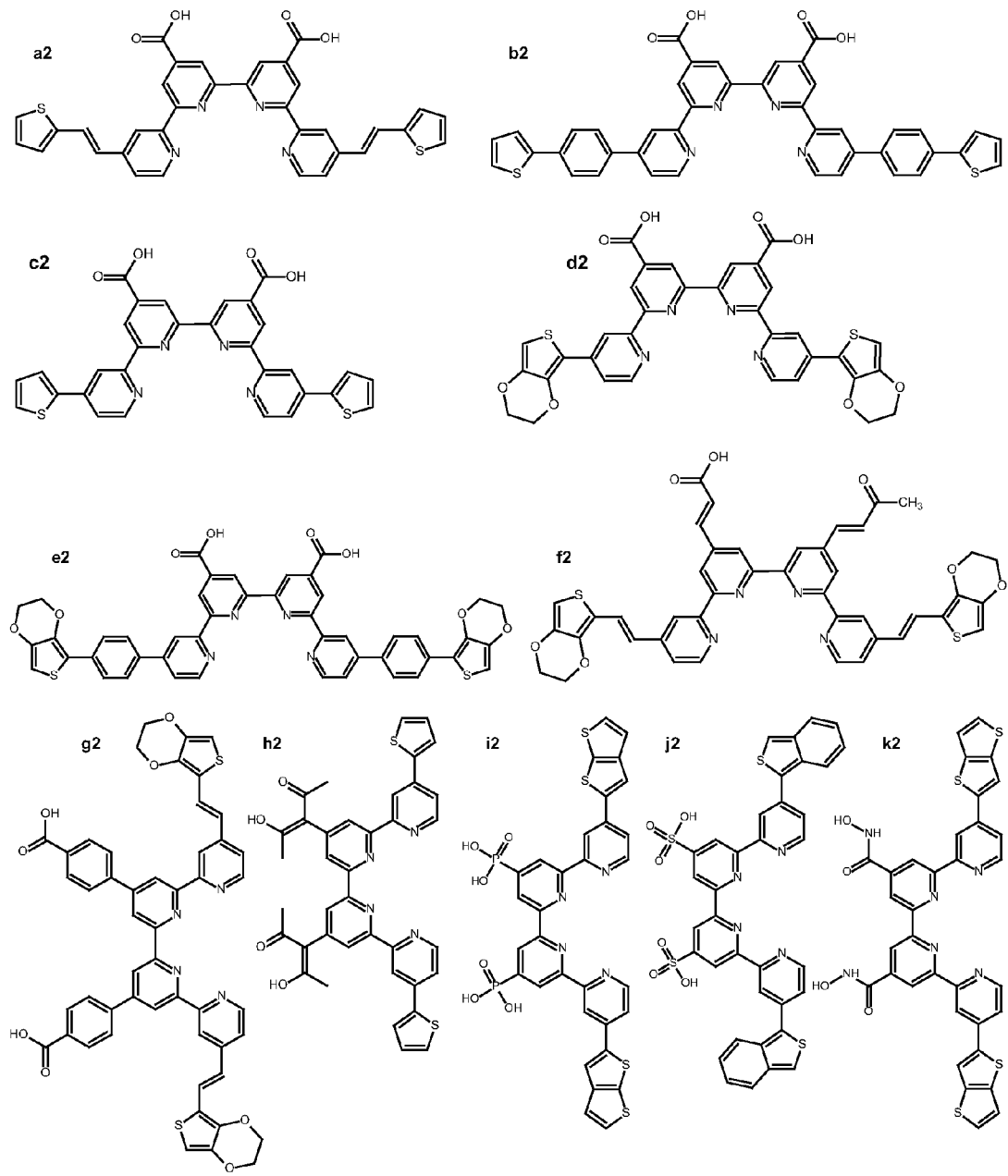
FIGS. 4a and 4b show exemplary quaterpyridine ligands a2-k2 and l2-q2, respectively, that can be used in sensitizing dyes for DSCs in accordance with the present invention.
Figure 4B:
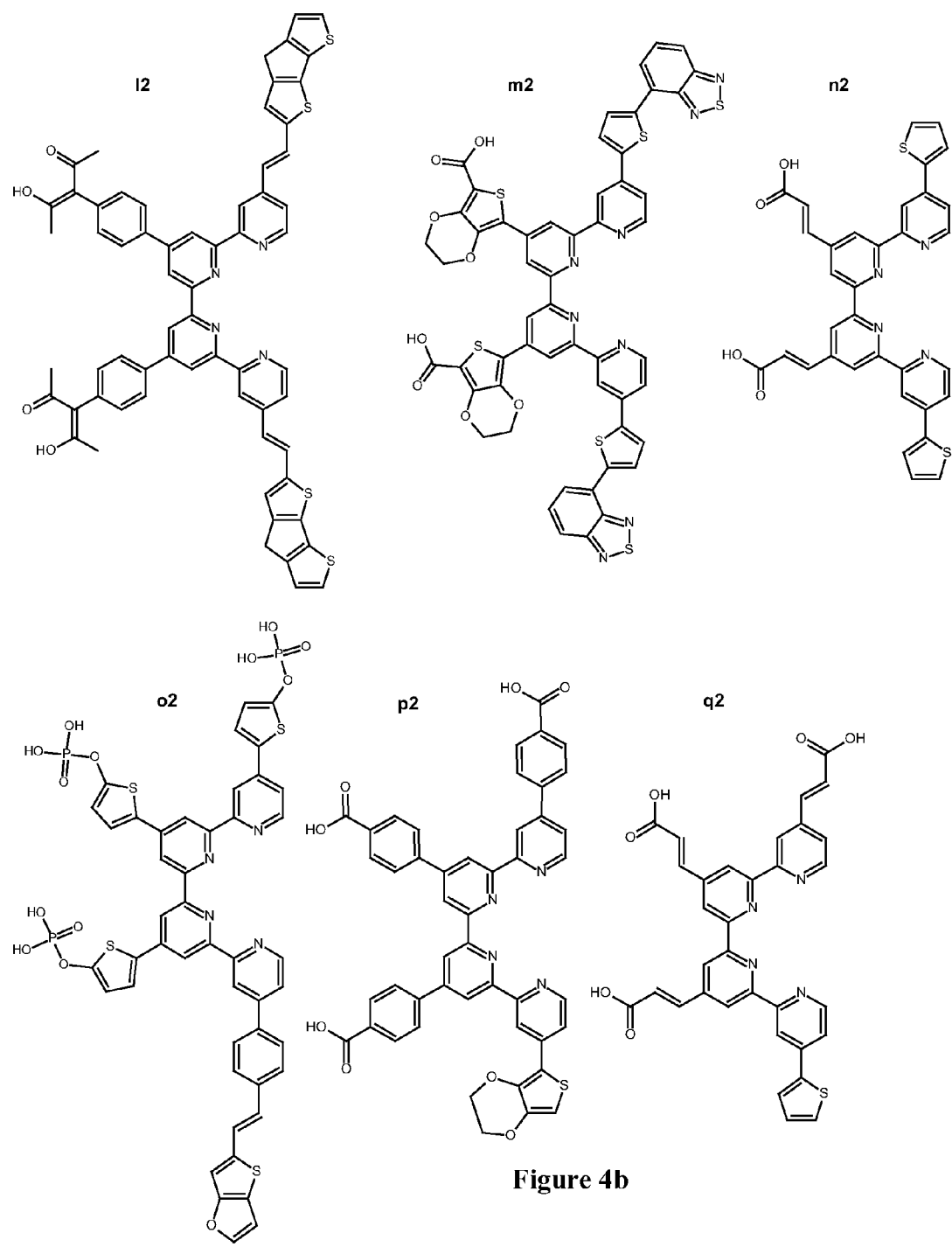

FIGS. 3 and 4 show structures of preferred embodiments of the compounds of the present invention. In particular, FIGS. 3a and 3b show exemplary embodiments of the bi-pyridine compounds of structure (IV), and FIGS. 4a and 4b show exemplary embodiments of the tetrapyridine compounds of structure (V).

In compounds a-l of FIG. 3a and compounds v-y of FIG. 3b, the anchoring substituent (—$R_{Anc}$) is constituted by a single —COOH group. In these compounds, n is thus 0. With respect to the substituent —$R_{Aryl}$, compounds a-y show various possibilities encompassed by the invention, in which m is 1 or 2. Compounds a1-i1 in FIG. 3b illustrate different anchoring groups.

In FIG. 3b, compound y represents a bipyridine compound comprising, in substituent $R_{Aryl}$, an embodiment of moiety (5) above, in which p=1 and $R^{13}$ and $R^{14}$ ($R^{97}$ and $R^{98}$ in compound y) are both attached to the same carbon.

In FIG. 4a, compounds a2-g2 are all symmetrical compounds with two substituents $R_{Anc}$ with —COOH as anchoring groups and two substituents $R_{Aryl}$, wherein n and m vary from 0-1 (n) and 1-2 (m), respectively. Compounds h2-l2 (extending to FIG. 4b) and o2 are compounds with anchoring groups other than —COOH. In compounds f2 and g2 and l2-q2, n is 1 and m is 1 or 2, with different anchoring groups being present in the different compounds. In all compounds shown in FIGS. 3 and 4, any $A_Z$ of $R_{Anc}$ and any $B_X$ of $R_{Aryl}$ is selected from is selected from moieties (1)-(30). In any $R_{Aryl}$, $R_{16}$ is —H.

According to various embodiments of the present invention, the compounds of the invention are used as ligands of organometallic compounds, and/or they are used as components of dyes. Preferably, the compounds are used as ligands in metal dyes that are useful as sensitizers. Such sensitizers or sensitizing dyes can be used in dye-sensitized photoelectric conversion devices, photoelectrochemical cells and/or in particular dye-sensitized solar cells (DSCs).

The invention thus also encompasses organometallic compounds, in particular dyes comprising the compounds of the invention.

The compounds of the invention can be used as ligands and combined with other ligands, if desired and as deemed useful by the skilled person. Preferred organometallic compounds are metal dyes comprising at least one metal atom, preferably as specified in the embodiments disclosed below. The compounds of the present invention provide specific characteristics to the entire dye, which can be combined the same ligand or other ligands having other characteristics as desired, and which thus have an impact of the properties of the entire dye comprising the compound of the invention.

According to an embodiment, the organometallic compound of the present invention comprises a formula selected from formula (X) and (XI) below as defined above.

$$M L_1 L_2 L_3 L_4 \qquad (X);$$

$$M L_5 L_3 L_4 \qquad (XI);$$

$L_3$ and $L_4$ are monodentate ligands. The monodentate ligands $L_3$ and $L_4$ may be selected from monodentate anionic ligands, for example, halide⁻ (such as I⁻, Cl⁻, Br⁻), CNS⁻ and CN,⁻ and monodentate non-charged ligands, for example substituted triaryl phosphines, mono-pyridines, imidazole and benzimidazole, for example.

M is preferably selected from ruthenium, osmium, rhodium, and iridium; preferably from ruthenium, osmium, rhodium and iridium, most preferably the metal is ruthenium;

Preferably, the bi-pyridine ligand of formula (XX) above comprises one or two anchoring ligands —$R_{Anc}$.

According to a preferred embodiment, said bi-pyridine of formula (XX) is a compound of formula (XXI) below:

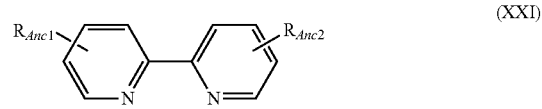

wherein $R_{Anc1}$ and $R_{Anc2}$ are independently selected from $R_{Anc}$ as defined above, and wherein the bi-pyridine of formula (XXI) is not further substituted.

Preferably, all anchoring ligands $R_{Anc}$ on the same pyridine structures (I), (IV), (V), (XX) and (XXI) are identical.

Further substituents of the bipyridine structure of formulae (XX) and (XXI) are independently defined as the further substituents defined above with respect to the compound of formula (I), (IV) and/or (V). Preferably, there are no further substituents besides the one or more substituent(s) —$R_{Anc}$.

The present invention further concerns a photoelectric conversion device comprising a compound of formula (I) and/or of the embodiments of this compound described above, and/or of a organometallic compound comprising the compound as a ligand. Preferably, the photoelectric conversion device comprises a sensitising dye as defined herein above, in particular a dye selected from the dyes of formula (X) and/or (XI).

Preferably, the photoelectric conversion device is a regenerative cell, preferably a regenerative DSC.

Figure 11:
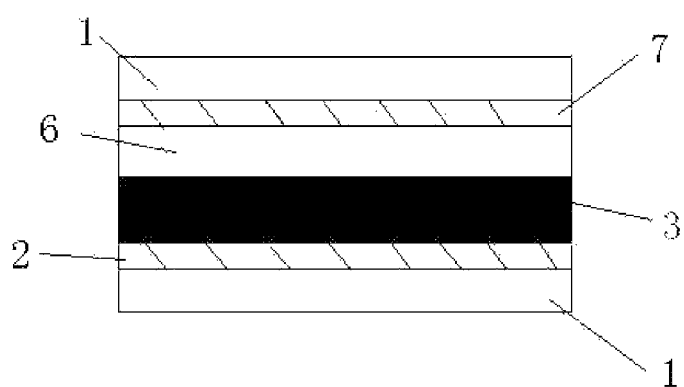
FIG. 11 shows an embodiment of a solar cell according to the invention. The cell comprises two support layers 1, at least one of which is transparent, a light absorption layer 3, a conductive layer 2, a counter electrode 7, and a charge transport layer 6.
Figure 12:
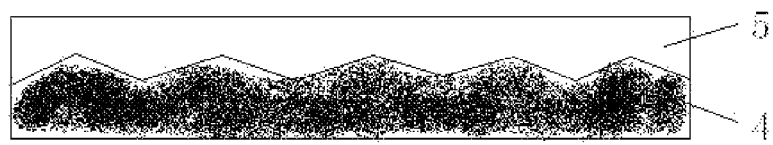
FIG. 12 shows in greater detail the light absorption layer 3 of FIG. 11. This layer is composed of a semiconductor nanoparticle layer 4 and of a dye layer 5. The dye layer 5 preferably comprises the dyes of the present invention and/or the compounds of the present invention.

FIGS. 11 and 12 show an embodiment of the dye-sensitized solar cell of the present invention.

According to an embodiment of the present invention, the photoelectric conversion device comprises a light absorption layer 3, which comprises a semiconductor material 4 and, absorbed thereto, a dye layer 5 comprising a dye according to the invention and/or a dye 5 comprising a compound according to the present invention.

According to an embodiment, the DSC of the present invention comprises one or two substrate layers 1, at least one of which is transparent. The substrate layers may be made from the same or from different materials. One or both substrate layers may function as support layers of the cell. The DSC further comprises a conductive layer 2, a light absorption layer 3, a charge transport layer 6 and counter electrode 7. Said conductive layer 2, said light absorption layer 3, said electrolyte layer 6 and said counter electrode 7 are preferably connected in this order, for example between two transparent substrate layers 1. The said semiconductor nanoparticle layer 4 is preferably electrically connected with the said conductive layer 2 and the said dyes layer 5 is in electrical contact with the said charge transport layer 6.

According to an embodiment, the photoelectrode comprises one or two semiconductor material films or layers, for example one or two mesoscopic, porous films layers. An example for a preferred semiconductor material is $TiO_2$. For example, the device comprises a photoelectrode comprising and/or consisting of a single one or two mesoscopic, porous semiconductor material layer(s), independently selected from layers having a thickness of 4-20 μm.

Preferably, the semiconductor material 4 provides at least part of a photoelectrode. The photoelectrode preferably comprises a nanocrystalline, porous layer of a semiconductor material, said porous layer being characterized by a roughness factor of larger than 20, preferably larger than 200 and even larger than 1000. Preferably, the photoelectrode is a photoanode. The photoelectrode and the counterelectrode are preferably provided on support substrates 1, such as transparent glass or plastic, at least one of which is transparent.

Electrode (photo- and counterelectrode) materials, including further semiconductor materials, and electrolytes that are suitable for the present invention are disclosed in EP1507307, WO2006/010290, WO2007/093961, and in many more. According to a preferred embodiment of the invention, the semiconductor material comprises a material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$. Devices containing electrically conductive charge transporting materials are disclosed in WO2007/107961. In the above references, the manufacturing of such devices is also disclosed. In FIG. 1 of EP1507307, an embodiment of a possible structure of devices of the present invention is disclosed. On page 8, line 10 to page 9, line 51, general information and suitable materials of the preparation of devices encompassed by the present invention is disclosed. Of course, the present invention is not limited to devices as disclosed in these references.

The invention is illustrated by the Examples below, which are not intended to limit the scope of the invention.

EXAMPLES

Examples 1-4 relate to the synthesis of compounds that are used as ligands and dyes according to the present invention. Example 5 sets out the preparation of dye-sensitized solar cells and of the methodology for determination of cell characteristics. Examples 6 and 7 set out the results obtained with the dyes of Examples 2 and 4, respectively.

Example 1

Figure 1:
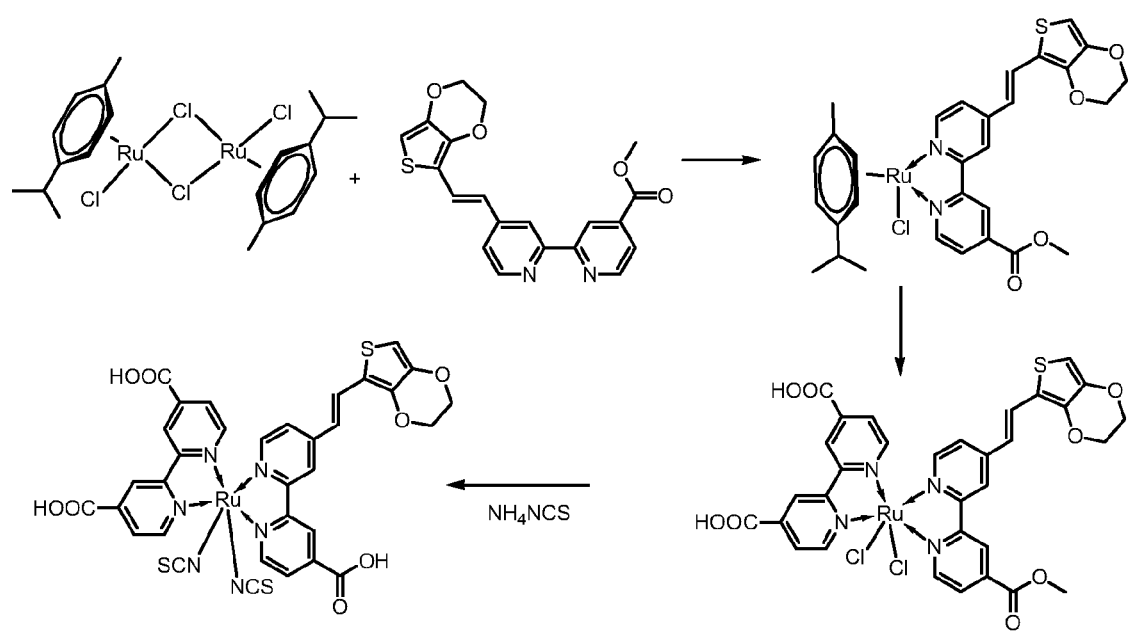

Synthesis of the Ligand 4-[2-(3,4-Ethylenedioxythien-2-yl)vinyl]-4'-methoxycarbonyl-2,2'-bipyridine (8) (Hydrolized Product of Precursor 8 Shown in FIG. 1a)

The synthesis of the bi-pyridine compound (8) and of the dye (7) are schematically illustrated in the scheme of FIGS. 1a and 1b.

a) 2-(2-Bromopyrid-4-yl)-1-(3,4-ethylenedioxythien-2-yl)ethanol (9)

4-Methyl-2-bromopyridine (450 mg, 2.62 mmol) was dissolved in anhyd THF (10 mL) and the resulting mixture was cooled to −78° C. LDA (1.76 mL, 1.8 M solution in THF, 3.17 mmol) was added dropwise and the resulting mixture was stirred for 1 h at the same temperature. A solution of 3,4-ethylenedioxythiophene-2-carboxaldehyde (500 mg, 2.94 mmol) in THF (20 mL) was added and the resulting mixture was stirred for 30 min at room temperature. AcOEt (120 mL) and water (120 mL) were added and the layers were separated. The organic layer was washed with water (2×150 mL), dried ($Na_2SO_4$) and the solvent was removed by rotary evaporation. Flash chromatography of the residue (silica gel, petroleum ether/AcOEt 1:1) afforded (9) as a yellow oil (850 mg, 2.48 mmol, 95%). $^1$H NMR (500 MHz, $CDCl_3$) δ 8.23 (d, J=5.0 Hz, 1H), 7.38 (s, 1H), 7.10 (d, J=5.0 Hz, 1H), 6.29 (s, 1H), 5.18 (t, J=6.7 Hz, 1H), 4.20-4.05 (m, 4H), 3.20-2.95 (m, 2H).

b) 2-Bromo-4-[2-(3,4-ethylenedioxythien-2-yl)vinyl]pyridine (10)

Compound (9) (800 mg, 2.34 mmol) was dissolved in pyridine (2 mL). $POCl_3$ (327 μL, 538 mg, 3.51 mmol) was added and the resulting mixture was cooled to −78° C. Upon addition of water (40 mL) the formation of a precipitate was observed. The cooling bath was removed and the mixture was stirred for 15 min. A precipitate was obtained which was collected upon filtration and washed with petroleum ether/ethyl acetate (20 mL, 1:1) affording pure (10) as a yellow solid (380 mg, 1.17 mmol, 50%), mp 127-129° C. $^1$H NMR (500 MHz, $CDCl_3$) δ 8.27 (d, J=5.2 Hz, 1H), 7.51 (s, 1H), 7.34 (d, J=16.1 Hz, 1H), 7.25 (d, J=5.2 Hz, 1H), 6.70 (d, J=16.1 Hz, 1H), 6.38 (s, 1H), 4.35-4.33 (m, 2H), 4.27-4.25 (m, 2H).

c) Methyl 2-(trimethylstannyl)isonicotinate (12)

Hexamethyldistannane (210 μL, 334 mg, 1.02 mmol) and tetrakis(triphenylphosphine)palladium(0) (70 mg, 0.06 mmol) were added to a solution of methyl 2-chloroisonicotinate (11) (100 mg, 0.58 mmol) in toluene (10 ml) and the resulting mixture was refluxed for 3 h. AcOEt (50 mL) and water (100 mL) were then added. The layers were separated and the organic layer was washed with water (5×100 mL), dried ($Na_2SO_4$), and the solvent removed by rotary evaporation to leave (12) as an oily residue which was used in the next step without further purification.

d) 4-[2-(3,4-Ethylenedioxythien-2-yl)vinyl]-4'-methoxycarbonyl-2,2'-bipyridine (8)

A solution of (12) (95 mg, 0.32 mmol) in toluene (5 mL) was added to a solution of (10) (105 mg, 0.32 mmol) in the same solvent (5 mL). Tetrakis(triphenylphosphine)palladium (0) (34 mg, 0.03 mmol) was added and the resulting mixture was refluxed for 20 min. A brown precipitate was obtained which was collected upon filtration, extensively washed with toluene, and dried under vacuum, yielding the product (8) (65 mg, 53%) which was directly used without further purification in the next step. $^1$H NMR (500 MHz, $CDCl_3$) δ 8.98 (s, 1H), 8.88 (d, J=4.9 Hz, 1H), 8.65 (d, J=5.1 Hz, 1H), 8.48 (s, 1H), 7.90 (d, J=4.2 Hz, 1H), 7.48 (d, J=16.1 Hz, 1H), 7.37 (d, J=4.4 Hz, 1H), 6.93 (d, J=16.2 Hz, 1H), 6.35 (s, 1H), 4.36-4.34 (m, 2H), 4.28-4.26 (m, 2H), 4.00 (s, 3H).

Example 2

Synthesis of the dye [Cis-(dithiocyanato)-Ru-(4,4'-dicarboxylate-2,2'-bpy)-[4-carboxylate-4'-[(E)-2-EDOTvinyl]-2,2'-bpy] (7)

A mixture of [{$RuCl_2$(p-cymene)}$_2$] (64 mg, 0.11 mmol) and Ligand (80 mg, 0.21 mmol) was vacuum-dried and added DMF (30 ml) and the reaction mixture was heated at 80° C. under nitrogen for 4 h. Then, bipyridyl(carboxylic acid) (51 mg, 0.21 mmol) was added to the solution and refluxed at 160° C. for another 4 h under dark condition. Excess of $NH_4NCS$ $30H_2O$ (96 mg, 1.26 mmol) was added to the reaction mixture and heated at 130° C. for further overnight (8 h). Thereafter, the solvent was removed using a vacuum distillation. Water was added to the resulting semisolid to remove excess $NH_4NCS$. The water-insoluble product was collected on a sintered glass crucible by suction filtration and washed with distilled water. Then, the crude complex was dissolved in a solution of tetrabutyl ammonium hydroxide in methanol, loaded on a Sephadex LH-20 (2×30 cm) column and eluted with methanol. The product solution was concentrated, then added 0.1M HNO3 till the solution pH 5. Insoluble product was collected by suction filtration, which is the expected product (compound 7 in FIG. 1a, also shown in FIG. 1b).

Example 3

Synthesis of the tetrapyridine ligand trans-dithiocynato [Ru(4,4'''-bis[(E)-2-(3,4-ethylenedioxythien-2-yl)vinyl]-4',4''-bis(methoxycarbonyl)-2,2':6',2'':6'',2'''-quaterpyridine)] (13)

Figure 2:
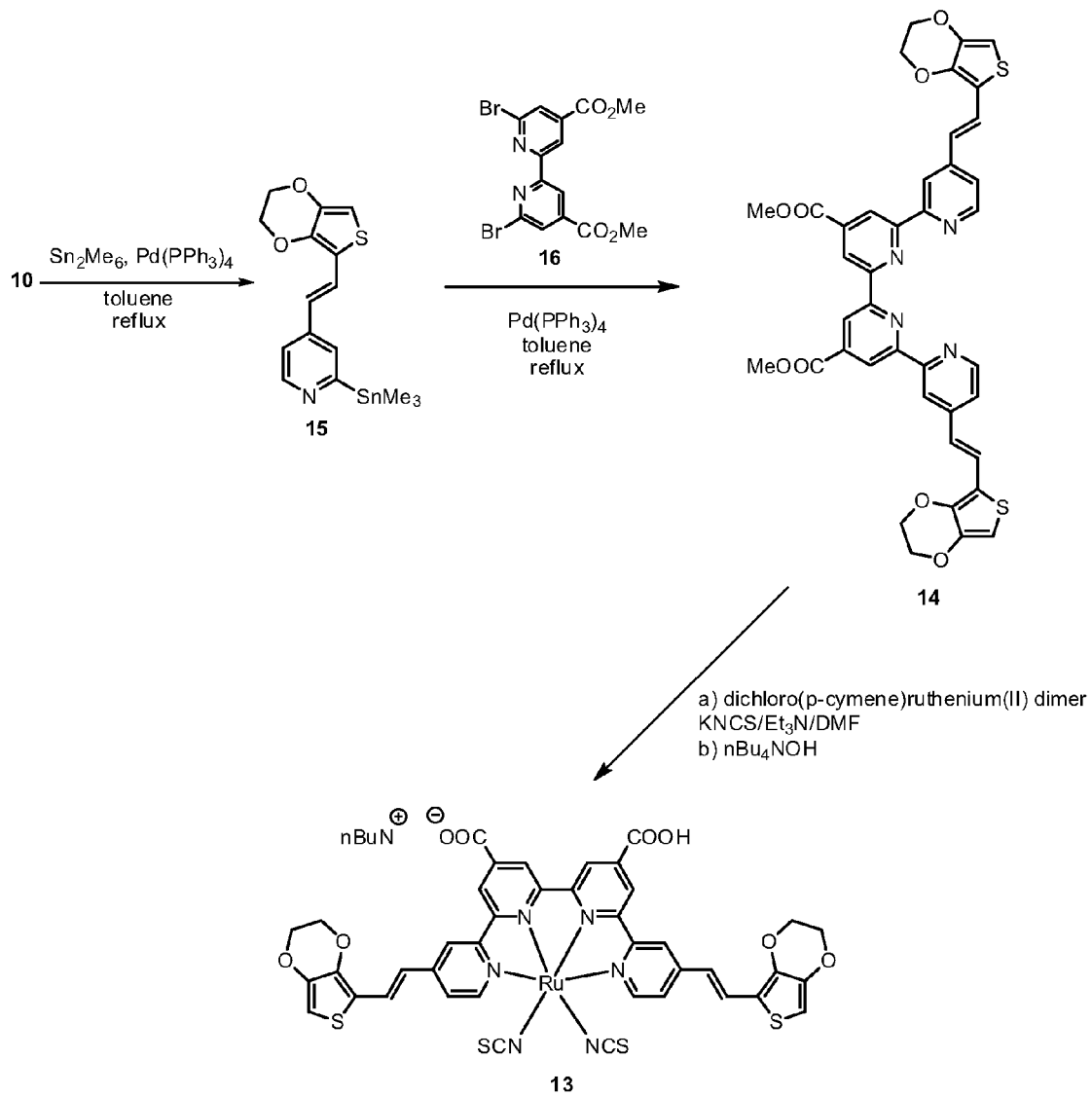
FIG. 2 shows the scheme of the synthesis of a tetra-pyridine ligand (compound 14) according to the invention and of a dye (compound 13) comprising the ligand, also according to the invention.

The synthesis of the quaterpyridine precursor compound (14) and of the dye (13) are schematically illustrated in the scheme of FIG. 2.

a) 4-[2-(3,4-Ethylenedioxythien-2-yl)vinyl]-2-(trimethylstannyl)pyridine (15)

Hexamethyldistannane (230 μl, 365 mg, 1.11 mmol) and tetrakis(triphenylphosphine)palladium(0) (20 mg, 0.017 mmol) was added to a solution of (10) (325 mg, 1.00 mmol) in anhyd toluene (20 mL) and the resulting mixture was refluxed for 12 h. Water (100 mL) and AcOEt (100 mL) were added and the layers were separated. The organic layer was washed with water (5×100 mL), dried ($Na_2SO_4$), and the solvent removed under reduced pressure to afford (15) as a colourless oil (355 mg, 0.87 mmol, 87%) which was used without further purification in the next step.

b) 4,4'''-Bis[2-(3,4-ethylenedioxythien-2-yl)vinyl]-4',4''-bis(methoxycarbonyl)-2,2':6',2'':6'',2'''-quaterpyridine (14)

4-[2-(3,4-Ethylenedioxythien-2-yl)vinyl]-2-(trimethylstannyl)pyridine (15) (355 mg, 0.87 mmol) and 6,6'-dibromo-4,4'-methoxycarbonyl-2,2'-bipyridine (16) (185 mg, 0.43 mmol) were dissolved in degassed anhyd toluene (20 mL). Tetrakis(triphenylphosphine)palladium(0) (10 mg, 0.009 mmol) was added and the resulting mixture refluxed for 18 h. After cooling to room temperature a solid was obtained which was collected upon filtration and extensively washed with dichloromethane, ethylacetate and acetone to yield (14) as a pale yellow powder (140 mg, 0.18 mmol, 42%). 1H NMR (500 MHz, DMSO) δ 9.09 (s, 2H), 8.95 (s, 2H), 8.72 (d, J=5.1, 2H), 8.61 (s, 2H), 7.62 (d, J=5.0 Hz, 2H), 7.55 (d, J=16.1 Hz, 2H), 7.03 (d, J=16.0 Hz, 2H), 6.73 (s, 2H), 4.42-4.38 (m, 4H), 4.31-4.26 (m, 4H), 4.09 (s, 6H); MS m/z 759 [M+H]$^+$.

Example 4

Synthesis of the tetrapyridine ligand trans-dithiocynato [Ru(4,4'''-bis[(E)-2-(3,4-ethylenedioxythien-2-yl)vinyl]-4',4''-bis(methoxycarbonyl)-2,2':6',2'':6'',2'''-quaterpyridine)] (13)

A mixture of 4,4'''-bis[2-(3,4-ethylenedioxythien-2-yl)vinyl]-4',4''-bis(methoxycarbonyl)-2,2':6',2'':6'',2'''-quaterpyridine (14) (0.140 g, 0.18 mM) and dichloro(p-cymene)ruthenium(II) dimer (0.056 g, 0.09 mM) in argon degassed DMF (50 mL) was heated at 140° C. for 4 h under reduced light. After this was added a solution of KNCS (0.8 g, 8.2 mM, dissolved in 2 mL of water). The reaction mixture was heated for further 5-6 h at 130° C. Then, 10 mL of triethylamine and 5 mL of $H_2O$ were added and the solution refluxed for 24 hours to hydrolyze the ester groups on the quaterpyridine ligand. The DMF solvent was evaporated, water (15 mL) was added to the resulting residue, and the mixture was let stand in a refrigerator overnight at −8° C. The resulting solid was then filtered and successively washed with water and diethyl ether to afford (13) (0.173 mg). The crude complex (13) was dissolved in methanol (5 mL) containing two equivalents of tetrabutylammonium hydroxide to confer solubility by deprotonating the carboxylic group. The concentrated solution was filtered through a sintered glass crucible (G4) and charged onto a Sephadex LH-20 column, which was prepared in methanol. The adsorbed complex was eluted using methanol. The main band was collected and the solution pH was lowered to 3.1 using 0.02 M $HNO_3$ acid. Then, the solution containing the precipitate was kept at −8° C. for 15 hours. After allowing the flask to warm up to 25° C., the precipitated complex was collected on a glass frit and air-dried. The same purification procedure was repeated two more times to obtain the pure N-bonded isomer complex. The NMR of the three times purified (13) shows the presence of only one isomer containing N-bonded NCS ligands 98.5% pure with one tetrabutylammonium cation.

Example 5

Device Fabrication and Photovoltaic Characterisation a) Device Fabrication

A screen-printed double layer thick film of interconnected $TiO_2$ particles on NSG10 TCO glass (Nippon Sheet Glass) was used as photo-anode. In particular, a double layer photo-anode configuration of anatase $TiO_2$ was used. A transparent layer of 8 μm thickness, composed of 20 nm anatase $TiO_2$ particles, was sheltered by a more diffusive/reflective layer of ca. 6 μm thickness (Dyesol DSL 18NR-AO) that enrolls small and scattering particles.

Electrodes were sensitized for 12 hours in a solution containing a concentration of ca. 250 μM of dye (compounds 7 or 13, respectively) in DMF and an equivalent proportion of cheno-deoxycholic acid as de-aggregating agent. After being washed by acetonitrile and dried under air flow, the sensitized electrodes were assembled with the counter electrode by melting a 25 μm thick Surlyn gasket. The Pt-loaded TEC15 TCO counter electrode was prepared by spreading out a drop of 5 mM ($H_2PtCl_6$) ethanolic solution and then heating the Pt-TCO at 400° C. during 15 min under air. The internal space between the working (i.e. photo-anode) and the counter electrodes was filled with volatile tbp-free A6979 electrolyte using a vacuum back filling system (0.6 M BMII, 0.1 M LiI, 0.05 M $I_2$ in acetonitrile/valeronitrile 85/15% by volume). The hole, prior made by sand-blasting, was clogged-up with a melted surlyn sheet.

b) UV-vis and Differential Cyclic Voltamperometry

UV-vis spectra were collected on a cary 5 spectrophotometer using a 1 cm path length quartz cells containing a $10^{-5}$ mol/L dye concentration in DMF. Electrochemical data were recorded using an Autolab potentiostat/galvanostat PGSTAT 30. For this, the Differential Pulse Voltamperogram (DPV) experiments were realized using three electrodes of Pt while Fc was used as internal reference. All these electrochemical measurements were realized in presence of 0.1 M TBA.PF$_6$ electrolyte support salt in DMF.

c) Photovoltaic Characterization

A 450 W xenon light source (Oriel, USA) was used to provide an incident irradiance of 100 mW/cm$^2$ at the surface of the solar cell. The spectral output of the lamp was filtered using a Schott K113 Tempax sunlight filter (Prazisions Glas & Optik GmbH, Germany). Light mismatch between real solar illumination and the simulated one was evaluated to be less than 2%. Light intensities were regulated with wire mesh attenuators. The (J-V) measurements were performed using a Keithley model 2400 digital source meter by applying independently external voltage to the cell and by measuring the photo-generated current supplied. Incident Photon-to-current Conversion Efficiency (IPCE) measurements were realized using a 300 W xenon light source (ILC Technology, USA). A Gemini-180 double monochromator Jobin Yvon Ltd. (UK) was used to select and increment wavelength irradiation to the cell.

d) Computational Studies

We use a combined computational approach in which the geometries of the dyes adsorbed onto TiO$_2$ are fully optimized using the Car-Parrinello (CP) method. In this stage we use the PBE functional together with a Plane Wave basis set and ultrasoft pseudopotentials for the description of core electrons. The CP program is freely distributed as part of the Quantum Espresso package (www.quantumespresso.org). The dyes have been optimized by the B3LYP functional and a 3-21G* basis set, in conjunction with a C-PCM solvation model, as implemented in the Gaussian03 (G03) program package. The G03 program is a commercially available software (Gaussian Inc., www.gaussian.com). Absorption spectra are computed by Time Dependent DFT, using the same B3LYP functional and solvation model used for geometry optimizations, and the larger DZVP basis set. Calculated vertical excitation energies have been convoluted by a set of gaussian functions with fixed broadening ($\delta=0.2$ eV).

Example 6

Results Obtained with Dye 7

Figure 5:
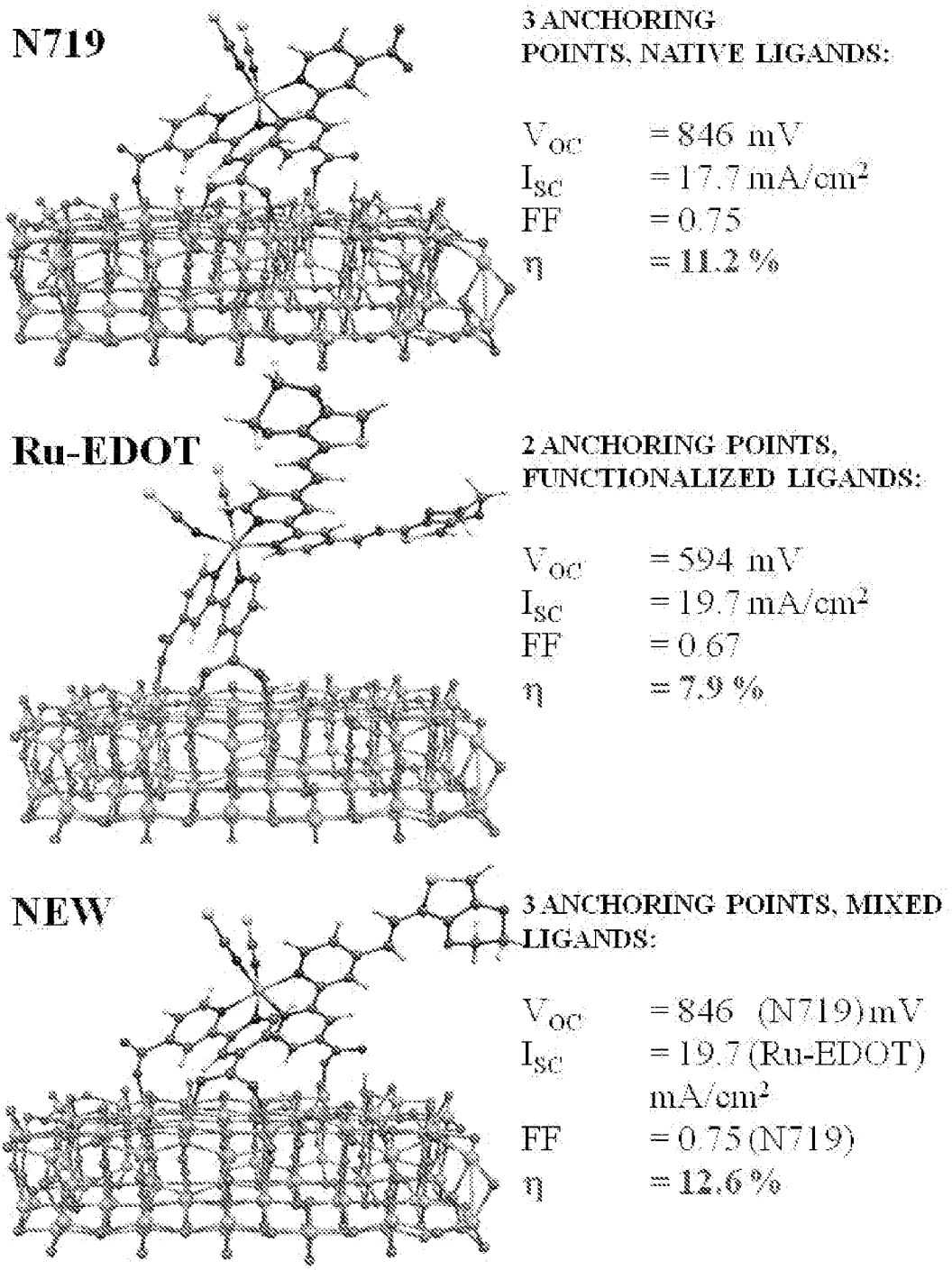
FIG. 5 shows the result of a computational simulation comparing different adsorption modes and the photovoltaic characteristics of the previously developed dyes (N719 and Ru-EDOT) with dye 7 (or compound 7) of the present invention (NEW). It can be seen that dye 7 of the invention achieves superior conversion efficiency (η=12.6%) if compared to the other dyes.

Results of the computational analysis obtained with dye 7 and dyes of the prior art are shown in FIG. 5. The analysis shows that the sensitizer anchoring mode onto TiO$_2$ and the control of the number of sensitizer protons are responsible for the higher open circuit voltage exhibited by the N719 dye compared to the vast series of heteroleptic dyes. FIG. 5 compares the adsorption mode, as determined by large-scale first principles DFT calculations, and the photovoltaic characteristics of the prototypical N719 and of the Ru-EDOT dye. N719 is characterized by three anchoring points to TiO$_2$ via three carboxylic groups residing on both bipyridines (accompanied by transfer of the sensitizer protons to the semiconductor surface) while the Ru-EDOT, as most of the other heteroleptic dyes, is adsorbed by using only two carboxylic acid groups residing on the same bipyridine.

It is clearly shown that while in the Ru-EDOT case one is able to increase the photocurrent compared to N719, a drastic reduction of the open circuit potential is measured compared to the latter dye, most likely due to the unfavorable sensitizer dipole exerted onto the TiO$_2$ surface, which in turns leads to a downshift of the TiO$_2$ conduction band edge. Moreover, the three negatively charged carboxylic groups adsorbing onto TiO$_2$ in N719 can also lead to a larger conduction band up shift compared to adsorption of only two carboxylic groups in heteroleptic dyes.

The adsorption mode of the preferred compound, which possesses a structure corresponding to compound (7) is shown in the lower panel of FIG. 5. FIG. 5 shows that the same adsorption mode as the N719 dye would be maintained by the preferred compound of general compound (7), bearing both a carboxylic and a π-conjugated substituent, and a standard di-carboxylic bipyridine. By extrapolating values obtained from the N719 and the Ru-EDOT dyes we predict that the preferred compound of general compound (7) may exhibit solar to electric power conversion efficiencies exceeding 12%.

Figure 6:
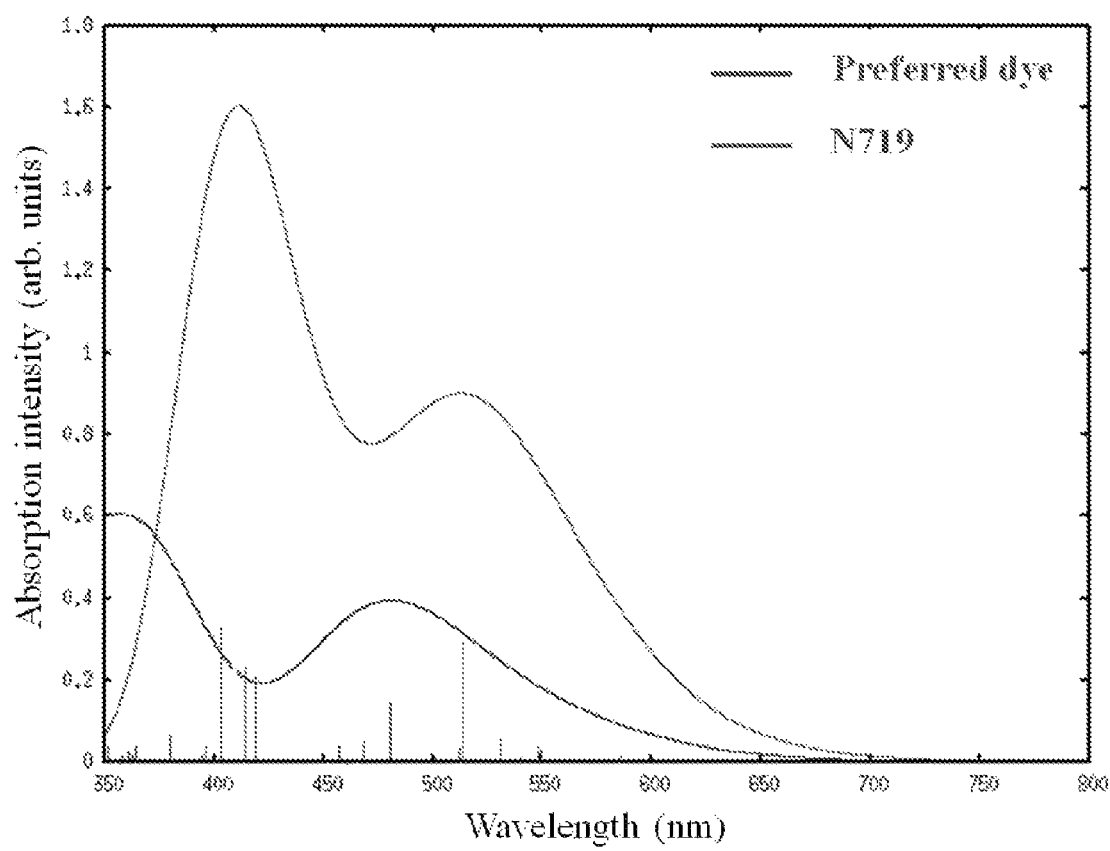
FIG. 6 shows simulated absorption spectra of dye 7 ("Preferred dye") and of the prior art dye N719 (lower line). Both dyes were considered as fully deprotonated species. The absorption spectrum of the preferred dye shows main transitions in the visible region which are red shifted and more intense than the corresponding ones of the N719 dye. This can explain the desired increased photovoltaic performances.

The simulated absorption spectra of the preferred compound and of the prototype N719 dye are compared in FIG. 6. To make a comparison independent from the protonation state of the two dyes, we investigated the fully deprotonated species, with overall charges −3 and −4 (preferred dye and N719, respectively). The absorption spectrum of the fully deprotonated N719 is, as previously reported in excellent agreement with the experimental data. The absorption maxima are computed within less than 0.1 eV compared to the experiment. A similar accuracy has been retrieved for the absorption spectrum of the Ru-EDOT dye, so we are fully confident that the simulated results of the preferred dye are a faithful representation of the complex absorption spectrum within 10% deviation with respect to the band positions, while the intensity should be, based on previous experience, accurate to within 30% compared to the experiment. As it can be noticed in FIG. 6, the absorption spectrum of the preferred dye shows main transitions in the visible region which are red shifted and more intense than the corresponding ones of the N719 dye. Considering their similar MLCT character, mixed in the preferred dye with some heteroaromatic substituent contribution, these results highlight the potentially superior light harvesting capability of the preferred dye compared to N719.

Example 7

Results Obtained with Dye 13 a) Opto-Electronic and Photovoltaic Properties

Figure 7:
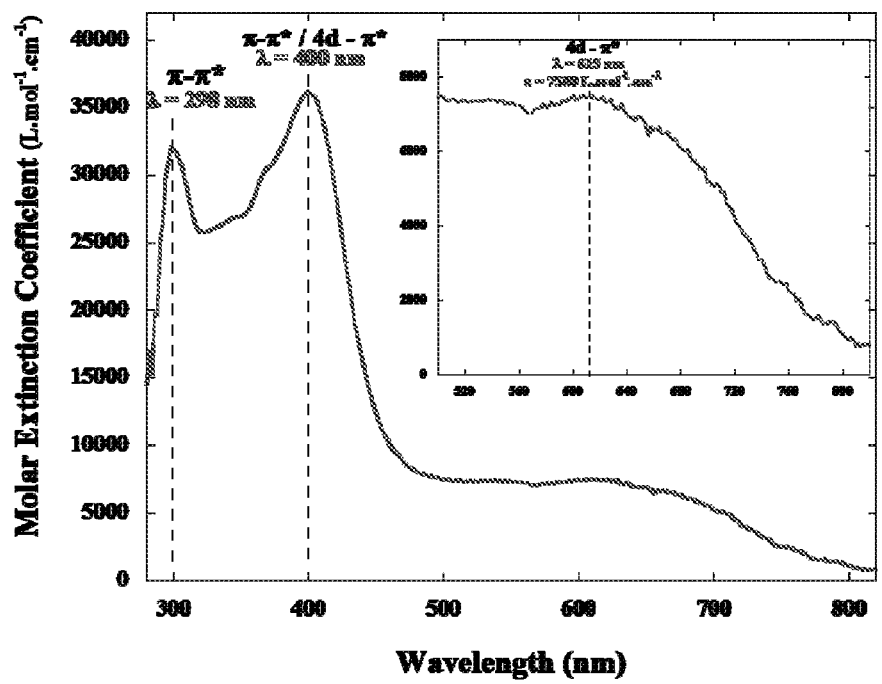
FIG. 7 shows the UV-Vis spectrum of dye trans-dithiocynato [Ru(4,4'''-bis[(E)-2-(3,4-ethylenedioxythien-2-yl)vinyl]-4',4''-bis(methoxycarbonyl)-2,2':6',2'':6'',2'''-quaterpyridine)] (the dye indicated as compound 13 in FIG. 2, shortly referred to as N1044 in DMF solvent. The inset shows an enlargement of the MLTC (metal-to-ligand charge-transfer).

As shown in FIG. 7, the incorporation of the 3,4-ethylenedioxythien-2-yl (EDOT) group attached to the quaterpyridine ligand, the UV-vis spectra recorded in DMF show three main contributions. The two first, located at 298 nm and 400 nm, originates from intra-ligand π-π* and the lowest MLCT 4d-π* transition, respectively. Interestingly, the second MLCT 4d-π* transition covers the entire visible range and reach a maximum at 615 nm with a molar extinction coefficient attaining 7500 L·mol$^{-1}$·cm$^{-1}$. The absorption broadness is very comparable to the so-called black dye (tri-thiocyanato-ruthenium(II) terpyridyl) and originates from the tetrapyridine ligand that gives rise to extend π conjugation and also likely to stabilize the trans configuration of the NCS donor group. On the other hand, it is also noteworthy the dye 13 (coded N1044) displays an increased molar extinction coefficient owing to the EDOT donor group with respect to the other reported tripyridine and tetrapyridine ligand.

Figure 8:
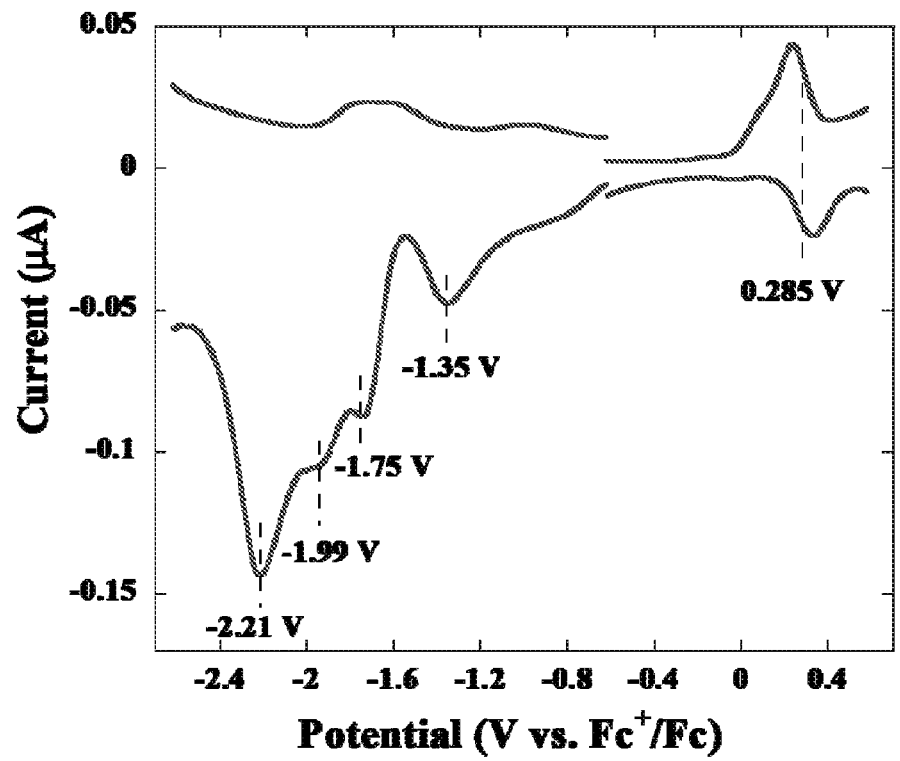
FIG. 8 shows the Differential Pulse Voltamperogram (DPV) of dye 13 (compound 13) in DMF solvent using 0.1 M $TBA.PF_6$ salt support electrolyte.

The achievement in the increase of the red-absorption ability is also confirmed from an electrochemical point of view. As shown by the differential pulse voltamperogram in FIG. 8, the HOMO level of the dye, which corresponds to the one electron Ru$^{+III}$/Ru$^{+II}$ redox system, is positioned at E$_{eq}$=+ 0.285 V (vs. Fc$^+$/Fc) with a quasi-reversible feature. This is particularly lower than the HOMO position of the N3 complex [+0.45 V (vs. Fc$^+$/Fc)] for instance and highlight the surprising benefit of introducing this electron rich heteroaromatic EDOT donor rings to destabilize HOMO orbitals energy of the metal center. On the other hand, in reduction, four subsequent peaks are observed at −1.35 V, −1.75 V, −1.99 V and −2.21 V (vs. Fc$^+$/Fc). The first is due to reduction of protons on the carboxylic acid function. The three irreversible peaks are ascribed to the tetrapyridyl ligand unit. The first energetical gap between the HOMO and LUMO levels is evaluated to be 2.03 eV which corresponds to a transition of 610 nm. This value is well consistent with the UV-vis spectrum which shows an absorption maximum at $\lambda_{(MLCT)}$=615 nm. This is also notably lower than the 2.47 eV obtained for our last reported Ru-EDOT heteroleptic sensitizer (Abbotto A. et al., Chem. Commun., 2008). The significant stabilization of the π* orbitals owing to the tetradentate configuration combined with the destabilization of the Ru$^{+II}$t$_{2g}$ ground state provide therefore a successful red-shift of the absorption edge.

Figure 9:
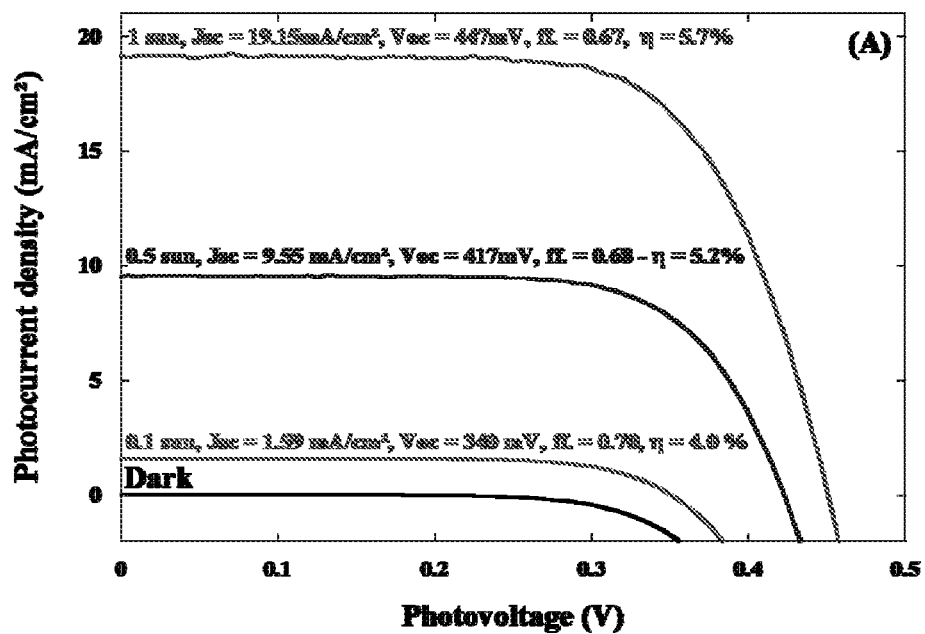
FIG. 9 shows the current-voltage characteristics of dye 13 determined in photoelectrochemical cells as produced in Examples 5 and discussed in Example 7, determined at different light intensities. It can be seen that at one equivalent sun illumination (100 mW/cm², A.M. 1.5 G) dye 13 delivers an excellent short circuit current density (JSC=19.15 mA/cm2) and a good fill factor (ff=67%).
Figure 10:
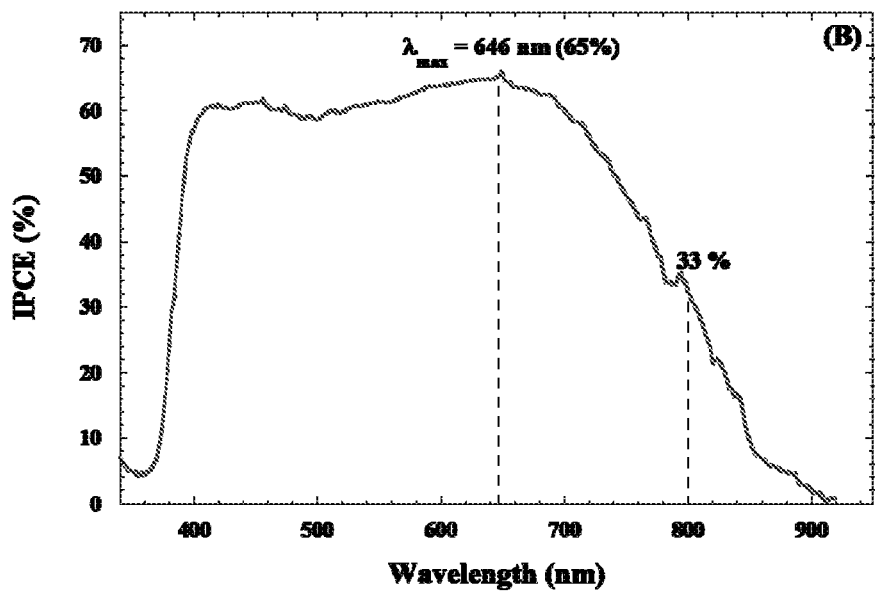
FIG. 10 shows the IPCE (Incident Photon-to-current Conversion Efficiency) of the same photoelectrochemical cell with dye 13 as in FIG. 8.

The photovoltaic performance of dye 13 (N1044) is shown in FIGS. 9 and 10. FIG. 9 presents the (J-V) curve recorded under different light illumination and FIG. 10 the corresponding Incident Photon-to-electron Conversion Efficiency (IPCE) spectrum. The photo-voltaic performance of dye 13 is reported in Table 1 below as a function of incident light illumination.

TABLE 1

Photovoltaic characteristics of dye 13 under different incident light intensity

| Light intensity | Jsc (mA/cm$^2$) | Voc (mV) | ff. | Efficiency (%) |
|---|---|---|---|---|
| 0.1 sun | 1.59 | 340 | 0.70 | 4.0 |
| 0.5 sun | 9.55 | 417 | 0.68 | 5.2 |
| 1 sun | 19.15 | 447 | 0.67 | 5.7 |

At one equivalent sun illumination (100 mW/cm$^2$, A.M. 1.5 G), dye 13 delivers an excellent short circuit current density as high as J$_{sc}$=19.15 mA/cm$^2$ and a good fill factor ff. of 67%. Nevertheless, the low cell Voc=447 mV penalties the overall cell performance leading to a photon-to-electron conversion efficiency of 5.7%. In agreement with the measured high current density and broad absorption in the visible range, the IPCE curve shows panchromatic response with a maximum of conversion obtained at 646 nm with ca. 65% IPCE and 33% still experienced at 800 nm. Note the absorption tail recorded until 910 nm. A bathochromic shift of about 30 nm is herein experienced as a consequence from the dye absorption onto the TiO$_2$ surface which entails the formation of carboxylate group as well as on the difference of salvation shell strength when using acetonitrile/valeronitrile-based electrolyte.

The invention claimed is:

1. A compound comprising a bipyridine structure of formula (IV) below:

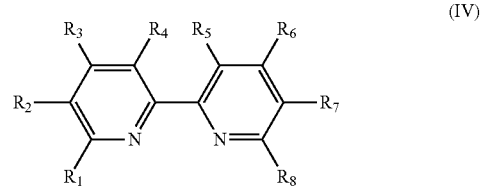

(IV)

wherein R$_3$ is a substituent R$_{Aryl}$ and R$_6$ is a substituent R$_{Anc}$;
wherein substituents R$_1$, R$_2$, R$_4$, R$_5$, R$_7$ and R$_8$ are H;
wherein R$_{Anc}$ is a substituent of formula (II) below:

(II)

wherein
n is 0 or an integer of 1;
Anc is an anchoring group selected from —COOH, —PO$_3$H$_2$, —SO$_3$H$_2$, —CONHOH$^-$, acetylacetonate;
A$_Z$ is independently selected from any moieties of formulae (1), (3) and (29) below:

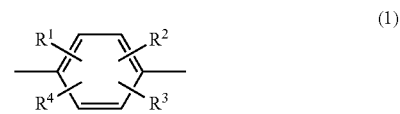

(1)

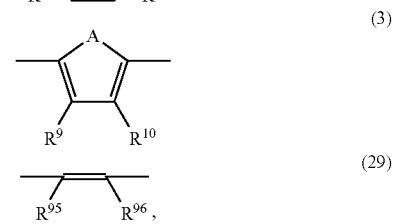

(3)

(29)

wherein:
A of the moiety of formulae (3) is a heteroatom selected from O, S and Se;
R$^1$-R$^3$, R$^9$-R$^{10}$ and R$^{95}$-R$^{96}$ are H; and
wherein R$_{Aryl}$ is selected from substituents of formula (VI) and (VII) below:

—B$_1$—R$_{16}$  (VI);

—B$_1$—B$_2$—R$_{16}$  (VII);

wherein:
B$_1$ of substituent (VI) is selected from any moieties of formulae (3), (4) and (5) below, B$_1$ of substituent (VII) is selected from any moieties of formulae (1), (2), (3), (4), (5), (29) and (30), and B$_2$ is selected from any moieties of formulae (3), (4), (5) below:

(1)

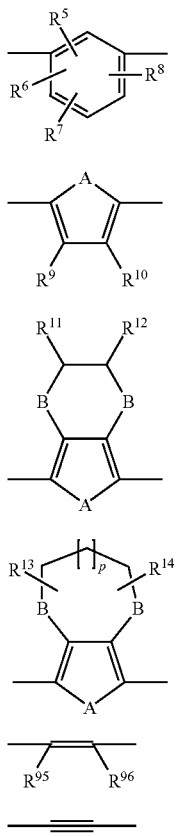

wherein:
A and B are a same or different heteroatom selected from O and S, in moiety (5), p is an integer of 1-2 and $R^{13}$ and $R^{14}$ may be bound to the same carbon atom,
any one of $R^1$-$R^{14}$ and $R^{95}$-$R^{96}$ are H; and
wherein $R_{16}$ is selected from H, halogen, —OH, C1-C5 alkyl, cyano group (—CN), and from C1-C5 alkoxyl.

2. The compound according to claim 1, wherein n is 0.

3. The compound according to claim 1, wherein
A in substituent $R_{Anc}$ of formula (II) is S atom;
A in substituents $R_{Aryl}$ of formula (VI) and of formula (VII) is S atom; and
B in substituent $R_{Aryl}$ of formula (VI) and of formula (VII) is O atom.

4. The compound according to claim 1, wherein
n of substituent $R_{Anc}$ of formula (II) is O;
A in substituent $R_{Aryl}$ of formula (VI) and of formula (VII) is S atom; and
B in substituent $R_{Aryl}$ of formula (VI) and of formula (VII) is O atom.

5. The compound according to claim 1, wherein
A in substituent $R_{Anc}$ of formula (II) is S atom;
$R_{Aryl}$ is selected from substituents of formula (VI) with A in substituents $R_{Aryl}$ of formula (VI) being S atom and with B in substituents $R_{Aryl}$ of formula (VI) being O atom.

6. The compound according to claim 1, wherein
A in substituent $R_{Anc}$ of formula (II) is S atom;
$R_{Aryl}$ is selected from substituents of formula (VII) with A in substituents $R_{Aryl}$ of formula (VII) being S atom and B of substituents $R_{Aryl}$ of formula (VII) being O atom.

7. The compound according to claim 1, wherein
n in substituent $R_{Anc}$ of formula (II) is 0 and Anc is —COOH;
$R_{Aryl}$ is selected from substituents of formula (VII), wherein $B_1$ is selected from moiety of formula (29) and $B_2$ is selected from moiety of formula (4) with A being S atom and B being O atom; and $R_{16}$ is H.

* * * * *